United States Patent
Charles et al.

(10) Patent No.: US 11,352,671 B2
(45) Date of Patent: Jun. 7, 2022

(54) PREDICTING THERAPEUTIC RESPONSE IN PARKINSON'S DISEASE

(71) Applicants: Vanderbilt University, Nashville, TN (US); Board of Trustees of Michigan State University, East Lansing, MI (US)

(72) Inventors: David Charles, Nashville, TN (US); Mallory Hacker, Nashville, TN (US); Caryl E. Sortwell, Grand Rapids, MI (US); Jack W. Lipton, Grand Rapids, MI (US)

(73) Assignees: VANDERBILT UNIVERSITY, Nashville, TN (US); BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 619 days.

(21) Appl. No.: 15/143,933

(22) Filed: May 2, 2016

(65) Prior Publication Data
US 2016/0319355 A1    Nov. 3, 2016

Related U.S. Application Data

(60) Provisional application No. 62/155,686, filed on May 1, 2015.

(51) Int. Cl.
*C12Q 1/68* (2018.01)
*C12Q 1/6883* (2018.01)
*G01N 33/68* (2006.01)

(52) U.S. Cl.
CPC ....... *C12Q 1/6883* (2013.01); *G01N 33/6896* (2013.01); *C12Q 2600/106* (2013.01); *C12Q 2600/156* (2013.01); *G01N 2333/475* (2013.01); *G01N 2800/2835* (2013.01); *G01N 2800/52* (2013.01)

(58) Field of Classification Search
None
See application file for complete search history.

(56) References Cited

U.S. PATENT DOCUMENTS

2005/0014170 A1 * 1/2005 Weinberger .......... C07K 14/475 435/6.11

OTHER PUBLICATIONS

Syka et al; PNAS, vol. 101, pp. 9528-9533, Jun. 2004.*
Foltynie et al; J. Neurol. Neurosurg. Psychiatry, Oct. 2008; vol. 80, pp. 141-144.*
Benabid et al; The Lancet; vol. 8, 2009, pp. 67-81.*
Schuepbach et al; The New England Journal of Medicine, vol. 368, 2013, pp. 610-622.*
Adler et al., "Low clinical diagnostic accuracy of early vs advanced Parkinson disease: Clinicopathologic study", *Parkinsonism Relat Disord* (2014).
Agundez et al., "Anti-Parkinson's disease drugs and pharmacogenetic considerations", *Expert Opin Drug Metab Toxicol*, 9(7): p. 859-74 (2013).
Chen et al., "Genetic variant BDNF (Val66Met) polymorphism alters anxiety-related behavior", *Science*, 314(5796): p. 140-3 (2006).
Fischer et al., *Mov. Disord.* 29: S438-S429 (2014).
Foltynie et al., "BDNF val66met influences time to onset of levodopa induced dyskinesia in Parkinson's disease", *J Neurol Neurosurg Psychiatry*, 80(2): p. 141-4 (2009).
Guillin et al., "BDNF controls dopamine D3 receptor expression and triggers behavioural sensitization", *Nature* 411: 86-89 (2001).
Hacker et al., "Outcomes in early stage Parkinson's disease patients may be influenced by the BDNF Val66Met polymorphism", American Neurological Association 13th Annual Meeting, Abstract 350052, presented Oct. 2014.
Kalinderi et al., "Pharmacological treatment and the prospect of pharmacogenetics in Parkinson's disease" *Int J Clin Pract*, 65(12): p. 1289-94 (2011).
Kocabas et al., "Brain-derived neurotrophic factor gene polymorphisms: influence on treatment response phenotypes of major depressive disorder", *Int Clin Psychopharmacol*, 26(1): p. 1-10 (2011).
Pecina et al., "Valence-specific effects of BDNF Val66Met polymorphism on dopaminergic stress and reward processing in humans", *J. Neurosci.* 34: 5874-5881 (2014).
Perkovic et al., "Association between the brain-derived neurotrophic factor Val66Met poly morphism and therapeutic response to olanzapine in schizophrenia patients", *Psychopharmacology*, 231(18): p. 3757-3764 (2014).
Shulman et al., "The clinically important difference on the unified Parkinson's disease rating scale", *Arch Neurol*, 67(1): p. 64-70 (2010).
Sortwell, "Subthalamic nucleus deep brain stimulation and brain derived neurotrophic factor", Apr. 2014 Medtronic presentation.
Spieles-Engemann et al., "Subthalamic nucleus stimulation increases brain derived neurotrophic factor in the nigrostriatal system and primary motor cortex", *J Parkinsons Dis*, 1(1): p. 123-136 (2011).
Zintzaras & Hadjigeorgiou, "The role of G196A polymorphism in the brain-derived neurotrophic factor gene in the cause of Parkinson's disease: a meta-analysis", *J Hum Genet*, 50(11): p. 560-6, (2005).
Magrinelli, Francesca, et al. "Pathophysiology of motor dysfunction in Parkinson's disease as the rationale for drug treatment and rehabilitation." *Parkinson's Disease* 2016 (2016).
Reichmann, Heinz, Paolo Barone, and Werner Poewe, "Progression of Parkinson's Disease and unmet needs in mid-to late-stage patients." *Eur Neurol Rev* 10 (2015): 182-8.

* cited by examiner

*Primary Examiner* — Jehanne S Sitton
(74) *Attorney, Agent, or Firm* — Parker Highlander PLLC

(57) ABSTRACT

Provided herein are methods and compositions for determining the susceptibility of Parkinson's disease patients to optimized drug therapy (ODT) and or deep brain stimulation (DBS) therapy.

6 Claims, 3 Drawing Sheets

PREDICTING THERAPEUTIC RESPONSE IN PARKINSON'S DISEASE

This application claims benefit of priority to U.S. Provisional Application Ser. No. 62/155,686, filed May 1, 2015, the entire contents of which are hereby incorporated by reference.

BACKGROUND OF THE INVENTION

1. Field of the Invention

The present invention relates generally to the fields of medicine, neurobiology, and genetics. More particularly, it concerns identifying Parkinson's disease patients who are likely to benefit from Deep Brain Stimulation (DBS) Therapy.

2. Description of Related Art

Oral levodopa and deep brain stimulation of the subthalamic nucleus (STN DBS) are the mainstay pharmacological and surgical therapies for Parkinson's disease (PD). The introduction of levodopa often leads to a brief period of dramatic efficacy known as the 'honeymoon' phase. This honeymoon rapidly ends with increasing medication requirements and the onset of motor fluctuations, beginning after four to six years of levodopa treatment for about 40% of patients (Ahlskog and Muenter, 2001). During mid- and late-stage PD, some patients elect to undergo STN DBS and often experience a marked improvement in motor function, quality of life and motor fluctuations referred to by some as a 'second honeymoon' (Tanner, 2013). Although generally effective in treating PD motor symptoms, clinical response is highly variable for both of these therapies. For example, early-stage PD subjects receiving equivalent levodopa dosages experience a magnitude of response ranging from a 100% improvement to a 242% worsening as assessed using the Unified Parkinson's Disease Rating Scale part III (UPDRS-III, motor sub score) (Hauser et al., 2009). In one of the largest clinical trials of STN DBS, late-stage PD subjects experienced improvements in UPDRS-III that ranged from 3% to 63% improvement (Weaver et al., 2012). In addition, in a recent clinical trial in mid-stage PD subjects comparing STN DBS to medical therapy, UPDRS-III scores in the STN DBS treatment group ranged from an 83% improvement to a 7% worsening, whereas in the medication arm UPDRS-III scores ranged from a 50% improvement to a 42% worsening (Schuepbach et al., 2013. These reports underscore the heterogeneity in patient response to therapies and confirm that the clinical phenomenology of PD is extremely variable and patient-specific within each disease stage.

Preclinical studies show that both chronic levodopa administration and STN DBS result in alterations in brain-derived neurotrophic factor (BDNF) levels (Guillin et al., 2001; Spieles-Engemann et al., 2011; Fischer et al., 2014). These findings raise questions regarding whether BDNF levels contribute to patient response to antiparkinsonian therapies. A relatively common and functional single nucleotide substitution in the gene Bdnf (G>A results in Val66Met substitution in the protein BDNF; reference cluster ID: rs6265) has a prevalence of 40.6% in the human population (Val/Met 35.4%, Met/Met 5.2%, allelic frequency assuming Hardy-Weinberg) (dbSNP). Both the heterozygous major allele (Val/Met) and homozygous minor allele (Met/Met) of the Bdnf variant rs6265 result in disrupted packaging and release of activity-dependent BDNF (Chen et al. 2006). Since the majority of BDNF in the brain is released from neurons via this regulated secretory pathway, the Val/Met or Met/Met genotypes exhibit a significant decrease in available BDNF.[10] However, there is no information on whether BDNF rs6265 SNP genotype confers a differential response to either optimized drug therapy (ODT) or STN DBS plus medication (DBS) in early PD subjects.

SUMMARY OF THE INVENTION

Thus, in accordance with the present disclosure, there is provided a method of identifying a Parkinson's disease patient as a long-term responder to optimized drug therapy (ODT) and deep brain stimulation (DBS) therapy comprising (a) subjecting a nucleic acid-containing sample from a Parkinson's disease patient to sequence analysis; (b) determining the presence or absence of a single nucleotide polymorphism resulting in a Val→Met substitution in the brain derived neurotrophic factor (BDNF) gene coding for residue 66; and (c) identifying a patient as a long-term responder to both ODT and DBS when said nucleic acid-containing sample exhibits a Val/Val profile, and identifying a patient as a non-long-term responder to ODT when said nucleic acid-containing sample exhibits a Val/Met or met/met profile.

The method may further comprise treating said subject with ODT or DBS when said nucleic acid-containing sample exhibits a Val/Val profile, and/or may further comprise treating said subject with DBS when said nucleic acid-containing sample exhibits a Val/Met or met/met profile, and/or may further comprise treating said subject with ODT and DBS when said nucleic acid-containing sample exhibits a Val/Val profile. The patient may be an early stage Parkinson's disease patient. The long-term responder may be responding to ODT at 24 months following initiation of ODT.

The nucleic acid-containing sample may be a DNA sample, or an RNA sample. The nucleic acid-containing sample may be a tissue sample including, but not limited to, urine, cerebrospinal fluid, saliva, serum, skin, biopsy, biopsy of any organ, blood, semen, stool, ova, hair, hair follicle, or a mucosal cell. The sequence analysis may comprise PCR, comprises primer extension, site specific amplification, site specific hybridization, site specific cleavage, ligation, pyro-sequencing, SNP microarray, mini-sequencing, RNA seq, real time sequencing, ion or torrent pH sensing. The method further comprise preparing a report corresponding to step (c), or as an alternative step (c).

In another embodiment, there is provided a method of identifying a Parkinson's disease patient as a long-term responder to optimized drug therapy (ODT) and deep brain stimulation (DBS) therapy comprising (a) subjecting a protein-containing sample from a Parkinson's disease patient to sequence analysis; (b) determining the presence or absence of a Val→Met substitution in brain derived neurotrophic factor (BDNF) at residue 66; and (c) identifying a patient as a long-term responder to both ODT and DBS when said protein-containing sample exhibits a Val/Val profile, and identifying a patient as a non-long-term responder to ODT when said protein-containing sample exhibits a Val/Met or Met/Met profile.

The method may further comprise treating said subject with ODT or DBS when said protein-containing sample exhibits a Val/Val profile, and/or further comprise treating said subject with DBS when said protein-containing sample exhibits a Val/Met or Met/Met profile, and/or further comprise treating said subject with ODT and DBS when said protein-containing sample exhibits a Val/Val profile. The patient may be an early stage Parkinson's disease patient.

The long-term responder may be responding to ODT at 24 months following initiation of ODT.

The protein-containing sample may be a tissue sample including, but not limited to, urine, cerebrospinal fluid, saliva, serum, skin, biopsy, biopsy of any organ, blood, semen, stool, ova, hair, hair follicle, or a mucosal cell. The sequence analysis may be an antibody-based assay. The sequence analysis may comprise mass spectrometry. The method further comprise preparing a report corresponding to step (c), or as an alternative step (c).

In still a further embodiment, there is provided a kit comprising a first nucleic acid probe, primer or primer pair for determining the presence or absence of an rs6265 Met allele. The kit may further comprise one or more of a polymerase, a ligase, a restriction enzyme, a buffer, instructions for use of said kit, or a label. Another embodiment involves a kit comprising an antibody for determining the presence or absence of a Val→Met substitution at residue 66 of brain derived neurotrophic factor. The kit may further comprise one or more of a support, a third antibody for detection of said first and/or second antibody, a buffer, instructions for use of said kit, or a label. Finally, there is provided a probe or primer having a sequence that hybridizes to or adjacent to an rs6265 Met allele or a rs6265 Val allele, and an antibody that binds selectively to an epitope comprising residue 66 of brain derived neurotrophic factor. The kits may also comprise instructions on how to perform the methods above, and may include appropriate positive and negative control reactants.

For the purpose of this application, early stage Parkinson's disease patients are defined as having idiopathic Parkinson's disease, on anti-parkinsonian medications less than four years, and without a history of motor fluctuations and/or dyskinesias."

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
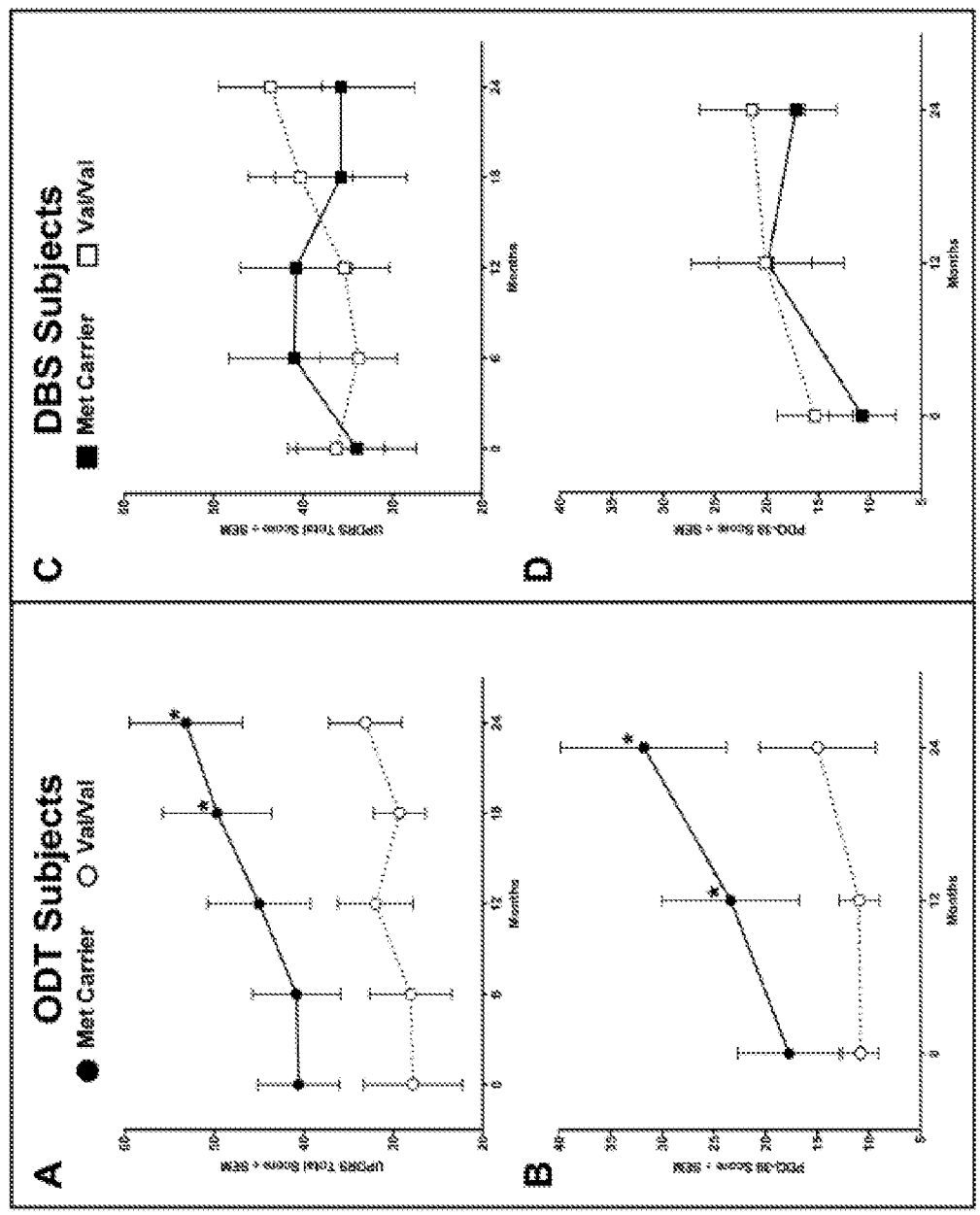
FIGS. 1A-D. Impact of the Bdnf variant rs6265 on UPDRS and PDQ-39 over 24 months after the Initiation of either DBS (DBS) or Optimized Drug Therapy (ODT). UPDRS. Met allele carriers in the ODT treatment arm exhibited significantly higher (worse) ON total UPDRS (total, ON medication) at 18 and 24 months compared to ODT subjects with only the more common variant (Val/Val, FIG. 1A, *, p=0.017 and p=0.019, respectively). PDQ-39. Met allele carriers in the ODT arm displayed significantly higher PDQ-39 scores at 12 and 24 months compared to Val/Val subjects in the ODT arm (FIG. 1B, *, p=0.033 and p=0.018, respectively). No significant differences were observed between Met allele carriers and Val/Val subjects receiving DBS at any time point (FIGS. 1C-D, p>0.05). Values represent the mean±SEM.

The inventors sought to determine whether the rs6265 single nucleotide polymorphism (SNP) in the brain derived neurotrophic factor (BDNF) gene confers a differential treatment response to either optimized drug therapy (ODT) or subthalamic nucleus deep brain stimulation (STN DBS) in early stage Parkinson's disease (PD) subjects. Response to ODT in subjects with the met allele (met66met or val66met) was significantly worse compared to normal (val66val) subjects. In contrast, both met allele and val66val subjects exhibited an equivalent response to STN DBS. Genotyping for the rs6265 met allele may be useful for predicting response to ODT and counseling patients when considering STN DBS. These and other details of the disclosure are described below.

I. Definitions

As used herein, an "allele" is one of a pair or series of genetic variants of a polymorphism at a specific genomic location. A "response allele" is an allele that is associated with altered response to a treatment. Where a SNP is biallelic, both alleles will be response alleles (e.g., one will be associated with a positive response, while the other allele is associated with no or a negative response, or some variation thereof).

As used herein, "genotype" refers to the diploid combination of alleles for a given genetic polymorphism. A homozygous subject carries two copies of the same allele and a heterozygous subject carries two different alleles.

As used herein, a "haplotype" is one or a set of signature genetic changes (polymorphisms) that are normally grouped closely together on the DNA strand, and are inherited as a group; the polymorphisms are also referred to herein as "markers." A "haplotype" as used herein is information regarding the presence or absence of one or more genetic markers in a given chromosomal region in a subject. A haplotype can consist of a variety of genetic markers, including indels (insertions or deletions of the DNA at particular locations on the chromosome); single nucleotide polymorphisms (SNPs) in which a particular nucleotide is changed; microsatellites; and minisatellites.

Microsatellites (sometimes referred to as a variable number of tandem repeats or VNTRs) are short segments of DNA that have a repeated sequence, usually about 2 to 5 nucleotides long (e.g., a CA nucleotide pair repeated three times), that tend to occur in non-coding DNA. Changes in the microsatellites sometimes occur during the genetic recombination of sexual reproduction, increasing or decreasing the number of repeats found at an allele, changing the length of the allele. Microsatellite markers are stable, polymorphic, easily analyzed and occur regularly throughout the genome, making them especially suitable for genetic analysis.

"Copy number variation" (CNV), as used herein, refers to variation from the normal diploid condition for a gene or polymorphism. Individual segments of human chromosomes can be deleted or duplicated such that the subject's two chromosomes carry fewer than two copies of the gene or polymorphism (a deletion or deficiency) or two or more copies (a duplication).

"Linkage disequilibrium" (LD) refers to when the observed frequencies of haplotypes in a population does not agree with haplotype frequencies predicted by multiplying together the frequency of individual genetic markers in each haplotype. When SNPs and other variations that comprise a given haplotype are in LD with one another, alleles at the different markers correlate with one another.

The term "chromosome" as used herein refers to a gene carrier of a cell that is derived from chromatin and comprises DNA and protein components (e.g., histones). The conventional internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3 \times 10^9$ base pairs.

The term "gene" refers to a DNA sequence in a chromosome that encodes a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing the same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of the hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably, at least partially, single stranded (e.g., denatured) at the time of hybridization. When the target nucleotide sequences are located only in a single region or fraction of a given chromosome, the term "target region" is sometimes used. Targets for hybridization can be derived from specimens that include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., Current Protocols in Molecular Biology, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

The term "SNP" stands for single nucleotide polymorphism, rs6265 in the brain derived neurotrophic factor gene.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30% (e.g., at least 40%, 50%, 60%, 70%, 80%, 90% or 100%) of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80% (e.g., 85%, 90%, 95%, 97% or more) identical.

The term "non-specific binding DNA" refers to DNA that is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, the term "stratification" refers to the creation of a distinction between subjects on the basis of a characteristic or characteristics of the subjects. Generally, in the context of clinical trials, the distinction is used to distinguish responses or effects in different sets of patients distinguished according to the stratification parameters. In some embodiments, stratification includes distinction of subject groups based on the presence or absence of particular markers or alleles described herein. The stratification can be performed, e.g., in the course of analysis, or can be used in creation of distinct groups or in other ways.

II. Parkinson's Disease

A. General Background

Parkinson's disease (PD, also known as idiopathic or primary parkinsonism, hypokinetic rigid syndrome/HRS, or paralysis agitans) is a degenerative disorder of the central nervous system. The motor symptoms of Parkinson's disease result from the death of dopamine-generating cells in the substantia nigra, a region of the midbrain; the cause of this cell death is unknown. Early in the course of the disease, the most obvious symptoms are movement-related; these include shaking, rigidity, slowness of movement and difficulty with walking and gait. Later, thinking and behavioral problems may arise, with dementia commonly occurring in the advanced stages of the disease, whereas depression is the most common psychiatric symptom. Other symptoms include sensory, sleep and emotional problems. Parkinson's disease is more common in older people, with most cases occurring after the age of 50.

The main motor symptoms are collectively called parkinsonism, or a "parkinsonian syndrome". Parkinson's disease is often defined as a parkinsonian syndrome that is idiopathic (having no known cause), although some atypical cases have a genetic origin. Many risk and protective factors have been investigated. The clearest evidence is for an increased risk of PD in people exposed to certain pesticides and a reduced risk in tobacco smokers. The pathology of the disease is characterized by the accumulation of a protein called alpha-synuclein into inclusions called Lewy bodies in neurons, and from insufficient formation and activity of dopamine produced in certain neurons within parts of the midbrain. Lewy bodies are the pathological hallmark of the idiopathic disorder, and the distribution of the Lewy bodies throughout the parkinsonian brain varies from one individual to another. The anatomical distribution of the Lewy bodies is often directly related to the expression and degree of the clinical symptoms of each individual. Diagnosis of typical cases is mainly based on symptoms, with tests such as neuroimaging being used for confirmation.

Modern treatments are effective at managing the early motor symptoms of the disease, mainly through the use of levodopa and dopamine agonists. As the disease progresses and dopaminergic neurons continue to be lost, these drugs eventually become ineffective at treating the symptoms and at the same time produce a complication called dyskinesia, marked by involuntary writhing movements. Diet and some forms of rehabilitation have shown some effectiveness at alleviating symptoms. Surgery and deep brain stimulation have been used to reduce motor symptoms as a last resort in severe cases where drugs are ineffective. Research directions include investigations into new animal models of the disease and of the potential usefulness of gene therapy, stem cell transplants and neuroprotective agents. Medications to treat non-movement-related symptoms of PD, such as sleep disturbances and emotional problems, also exist.

The term parkinsonism is used for a motor syndrome whose main symptoms are tremor at rest, stiffness, slowing of movement and postural instability. Parkinsonian syndromes can be divided into four subtypes according to their origin:
primary or idiopathic
secondary or acquired
hereditary parkinsonism, and
Parkinson plus syndromes or multiple system degeneration Parkinson's disease is the most common form of parkinsonism and is usually defined as "primary" parkinsonism, meaning parkinsonism with no external identifiable cause. In recent years several genes that are directly related to some cases of Parkinson's disease have been discovered. As much as this conflicts with the definition of Parkinson's disease as an idiopathic illness, genetic parkinsonism disorders with a similar clinical course to PD are generally included under the Parkinson's disease label. The terms "familial Parkinson's disease" and "sporadic Parkinson's disease" can be used to differentiate genetic from truly idiopathic forms of the disease.

Usually classified as a movement disorder, PD also gives rise to several non-motor types of symptoms such as sensory deficits, cognitive difficulties or sleep problems. Parkinson plus diseases are primary parkinsonisms which present additional features. They include multiple system atrophy, progressive supranuclear palsy, corticobasal degeneration and dementia with Lewy bodies.

In terms of pathophysiology, PD is considered a synucleiopathy due to an abnormal accumulation of alpha-synuclein protein in the brain in the form of Lewy bodies, as opposed to other diseases such as Alzheimer's disease where the brain accumulates tau protein in the form of neurofibrillary tangles. Nevertheless, there is clinical and pathological overlap between tauopathies and synucleinopathies. The most typical symptom of Alzheimer's disease, dementia, occurs in advanced stages of PD, while it is common to find neurofibrillary tangles in brains affected by PD.

Dementia with Lewy bodies (DLB) is another synucleinopathy that has similarities with PD, and especially with the subset of PD cases with dementia. However the relationship between PD and DLB is complex and still has to be clarified. They may represent parts of a continuum or they may be separate diseases.

B. Symptoms

Parkinson's disease affects movement, producing motor symptoms. Non-motor symptoms, which include autonomic dysfunction, neuropsychiatric problems (mood, cognition, behavior or thought alterations), and sensory and sleep difficulties, are also common. Some of these non-motor symptoms are often present at the time of diagnosis and can precede motor symptoms.

1. Motor

Four motor symptoms are considered cardinal in PD: tremor, rigidity, slowness of movement, and postural instability.

Tremor is the most apparent and well-known symptom. It is the most common; though around 30% of individuals with PD do not have tremor at disease onset, most develop it as the disease progresses. It is usually a rest tremor: maximal when the limb is at rest and disappearing with voluntary movement and sleep. It affects to a greater extent the most distal part of the limb and at onset typically appears in only a single arm or leg, becoming bilateral later. Frequency of PD tremor is between 4 and 6 hertz (cycles per second). A feature of tremor is "pill-rolling," the tendency of the index finger of the hand to get into contact with the thumb and perform together a circular movement. The term derives from the similarity between the movement in people with PD and the earlier pharmaceutical technique of manually making pills.

Bradykinesia (slowness of movement) is another characteristic feature of PD, and is associated with difficulties along the whole course of the movement process, from planning to initiation and finally execution of a movement. Performance of sequential and simultaneous movement is hindered. Bradykinesia is commonly a very disabling symptom in the early stages of the disease. Initial manifestations are problems when performing daily tasks which require fine motor control such as writing, sewing or getting dressed. Clinical evaluation is based in similar tasks such as alternating movements between both hands or both feet. Bradykinesia is not equal for all movements or times. It is modified by the activity or emotional state of the subject, to the point that some people are barely able to walk yet can still ride a bicycle. Generally people with PD have less difficulty when some sort of external cue is provided.

Rigidity is stiffness and resistance to limb movement caused by increased muscle tone, an excessive and continuous contraction of muscles. In parkinsonism the rigidity can be uniform (lead-pipe rigidity) or ratchety (cogwheel rigidity). The combination of tremor and increased tone is considered to be at the origin of cogwheel rigidity. Rigidity may be associated with joint pain; such pain being a frequent initial manifestation of the disease. In early stages of Parkinson's disease, rigidity is often asymmetrical and it tends to affect the neck and shoulder muscles prior to the muscles of the face and extremities. With the progression of the disease, rigidity typically affects the whole body and reduces the ability to move.

Postural instability is typical in the late stages of the disease, leading to impaired balance and frequent falls, and secondarily to bone fractures. Instability is often absent in the initial stages, especially in younger people. Up to 40% may experience falls and around 10% may have falls weekly, with number of falls being related to the severity of PD.

Other recognized motor signs and symptoms include gait and posture disturbances such as festination (rapid shuffling steps and a forward-flexed posture when walking), speech and swallowing disturbances including voice disorders, mask-like face expression or small handwriting, although the range of possible motor problems that can appear is large.

2. Neuropsychiatric

Parkinson's disease can cause neuropsychiatric disturbances which can range from mild to severe. This includes disorders of speech, cognition, mood, behavior, and thought.

Cognitive disturbances can occur in the initial stages of the disease and sometimes prior to diagnosis, and increase in prevalence with duration of the disease. The most common cognitive deficit in affected individuals is executive dysfunction, which can include problems with planning, cognitive flexibility, abstract thinking, rule acquisition, initiating appropriate actions and inhibiting inappropriate actions, and selecting relevant sensory information. Fluctuations in attention and slowed cognitive speed are among other cognitive difficulties. Memory is affected, specifically in recalling learned information. Nevertheless, improvement appears when recall is aided by cues. Visuospatial difficulties are also part of the disease, seen for example when the individual is asked to perform tests of facial recognition and perception of the orientation of drawn lines.

A person with PD has two to six times the risk of dementia compared to the general population. The prevalence of dementia increases with duration of the disease. Dementia is associated with a reduced quality of life in people with PD and their caregivers, increased mortality, and a higher probability of needing nursing home care.

Behavior and mood alterations are more common in PD without cognitive impairment than in the general population, and are usually present in PD with dementia. The most frequent mood difficulties are depression, apathy and anxiety. Establishing the diagnosis of depression is complicated by symptoms that often occur in Parkinson's including dementia, decreased facial expression, decreased movement, a state of indifference, and quiet speech. Impulse control behaviors such as medication overuse and craving, binge eating, hypersexuality, or pathological gambling can appear in PD and have been related to the medications used to manage the disease. Psychotic symptoms—hallucinations or delusions—occur in 4% of people with PD, and it is assumed that the main precipitant of psychotic phenomena in Parkinson's disease is dopaminergic excess secondary to treatment; it therefore becomes more common with increasing age and levodopa intake.

3. Other

In addition to cognitive and motor symptoms, PD can impair other body functions. Sleep problems are a feature of the disease and can be worsened by medications. Symptoms can manifest as daytime drowsiness, disturbances in REM sleep, or insomnia. Alterations in the autonomic nervous system can lead to orthostatic hypotension (low blood pressure upon standing), oily skin and excessive sweating, urinary incontinence and altered sexual function. Constipation and gastric dysmotility can be severe enough to cause discomfort and even endanger health. PD is related to several eye and vision abnormalities such as decreased blink rate, dry eyes, deficient ocular pursuit (eye tracking) and saccadic movements (fast automatic movements of both eyes in the same direction), difficulties in directing gaze upward, and blurred or double vision. Changes in perception may include an impaired sense of smell, sensation of pain and paresthesia (skin tingling and numbness). All of these symptoms can occur years before diagnosis of the disease.

C. Causes

Parkinson's disease in most people is idiopathic (having no specific known cause). However, a small proportion of cases can be attributed to known genetic factors. Other factors have been associated with the risk of developing PD, but no causal relationships have been proven.

1. Environmental Factors

A number of environmental factors have been associated with an increased risk of Parkinson's including: pesticide exposure, head injuries, and living in the country or farming. Rural environments and the drinking of well water may be risks as they are indirect measures of exposure to pesticides.

Implicated agents include insecticides, primarily chlorpyrifos and organochlorines and pesticides, such as rotenone or paraquat, and herbicides, such as Agent Orange. Heavy metals exposure has been proposed to be a risk factor, through possible accumulation in the substantia nigra; however, studies on the issue have been inconclusive.

2. Genetics

PD traditionally has been considered a non-genetic disorder; however, around 15% of individuals with PD have a first-degree relative who has the disease. At least 5% of people are now known to have forms of the disease that occur because of a mutation of one of several specific genes.

Mutations in specific genes have been conclusively shown to cause PD. These genes code for alpha-synuclein (SNCA), parkin (PRKN), leucine-rich repeat kinase 2 (LRRK2 or dardarin), PTEN-induced putative kinase 1 (PINK1), DJ-1 and ATP13A2. In most cases, people with these mutations will develop PD. With the exception of LRRK2, however, they account for only a small minority of cases of PD. The most extensively studied PD-related genes are SNCA and LRRK2. Mutations in genes including SNCA, LRRK2 and glucocerebrosidase (GBA) have been found to be risk factors for sporadic PD. Mutations in GBA are known to cause Gaucher's disease. Genome-wide association studies, which search for mutated alleles with low penetrance in sporadic cases, have now yielded many positive results.

The role of the SNCA gene is important in PD because the alpha-synuclein protein is the main component of Lewy bodies. Missense mutations of the gene (in which a single nucleotide is changed), and duplications and triplications of the locus containing it have been found in different groups with familial PD. Missense mutations are rare. On the other hand, multiplications of the SNCA locus account for around 2% of familial cases. Multiplications have been found in asymptomatic carriers, which indicate that penetrance is incomplete or age-dependent.

The LRRK2 gene (PARK8) encodes for a protein called dardarin. The name dardarin was taken from a Basque word for tremor, because this gene was first identified in families from England and the north of Spain. Mutations in LRRK2 are the most common known cause of familial and sporadic PD, accounting for approximately 5% of individuals with a family history of the disease and 3% of sporadic cases. There are many different mutations described in LRRK2, however unequivocal proof of causation only exists for a small number.

D. Pathology

1. Anatomical

The basal ganglia, a group of "brain structures" innervated by the dopaminergic system, are the most seriously affected brain areas in PD. The main pathological characteristic of PD is cell death in the substantia nigra and, more specifically, the ventral (front) part of the pars compacta, affecting up to 70% of the cells by the time death occurs.

Macroscopic alterations can be noticed on cut surfaces of the brainstem, where neuronal loss can be inferred from a reduction of neuromelanin pigmentation in the substantia nigra and locus coeruleus. The histopathology (microscopic anatomy) of the substantia nigra and several other brain regions shows neuronal loss and Lewy bodies in many of the remaining nerve cells. Neuronal loss is accompanied by death of astrocytes (star-shaped glial cells) and activation of the microglia (another type of glial cell). Lewy bodies are a key pathological feature of PD.

2. Pathophysiology

The primary symptoms of Parkinson's disease result from greatly reduced activity of dopamine-secreting cells caused by cell death in the pars compacta region of the substantia nigra.

There are five major pathways in the brain connecting other brain areas with the basal ganglia. These are known as the motor, oculo-motor, associative, limbic and orbitofrontal circuits, with names indicating the main projection area of each circuit. All of them are affected in PD, and their disruption explains many of the symptoms of the disease since these circuits are involved in a wide variety of functions including movement, attention and learning. Scientifically, the motor circuit has been examined the most intensively.

A particular conceptual model of the motor circuit and its alteration with PD has been of great influence since 1980, although some limitations have been pointed out which have led to modifications. In this model, the basal ganglia normally exert a constant inhibitory influence on a wide range of motor systems, preventing them from becoming active at inappropriate times. When a decision is made to perform a particular action, inhibition is reduced for the required motor system, thereby releasing it for activation. Dopamine acts to facilitate this release of inhibition, so high levels of dopamine function tend to promote motor activity, while low levels of dopamine function, such as occur in PD, demand greater exertions of effort for any given movement. Thus the net effect of dopamine depletion is to produce hypokinesia, an overall reduction in motor output. Drugs that are used to treat PD, conversely, may produce excessive dopamine activity, allowing motor systems to be activated at inappropriate times and thereby producing dyskinesias.

3. Brain Cell Death

There is speculation of several mechanisms by which the brain cells could be lost. One mechanism consists of an abnormal accumulation of the protein alpha-synuclein bound to ubiquitin in the damaged cells. This insoluble protein accumulates inside neurones forming inclusions called Lewy bodies. According to the Braak staging, a classification of the disease based on pathological findings, Lewy bodies first appear in the olfactory bulb, medulla oblongata and pontine tegmentum, with individuals at this stage being asymptomatic. As the disease progresses, Lewy bodies later develop in the substantia nigra, areas of the midbrain and basal forebrain, and in a last step the neocortex. These brain sites are the main places of neuronal degeneration in PD; however, Lewy bodies may not cause cell death and they may be protective. In people with dementia, a generalized presence of Lewy bodies is common in cortical areas. Neurofibrillary tangles and senile plaques, characteristic of Alzheimer's disease, are not common unless the person is demented.

Other cell-death mechanisms include proteosomal and lysosomal system dysfunction and reduced mitochondrial activity. Iron accumulation in the substantia nigra is typically observed in conjunction with the protein inclusions. It may be related to oxidative stress, protein aggregation and neuronal death, but the mechanisms are not fully understood.

E. Diagnosis

A physician will diagnose Parkinson's disease from the medical history and a neurological examination. There is no lab test that will clearly identify the disease, but brain scans are sometimes used to rule out disorders that could give rise to similar symptoms. People may be given levodopa and resulting relief of motor impairment tends to confirm diagnosis. The finding of Lewy bodies in the midbrain on autopsy is usually considered proof that the person had Parkinson's disease. The progress of the illness over time may reveal it is not Parkinson's disease, and some authorities recommend that the diagnosis be periodically reviewed.

Other causes that can secondarily produce a parkinsonian syndrome are Alzheimer's disease, multiple cerebral infarction and drug-induced parkinsonism.[42] Parkinson plus syndromes such as progressive supranuclear palsy and multiple system atrophy must be ruled out. Anti-Parkinson's medications are typically less effective at controlling symptoms in Parkinson plus syndromes. Faster progression rates, early cognitive dysfunction or postural instability, minimal tremor or symmetry at onset may indicate a Parkinson plus disease rather than PD itself. Genetic forms are usually classified as PD, although the terms "familial Parkinson's disease" and "familial parkinsonism" are used for disease entities with an autosomal dominant or recessive pattern of inheritance.

Medical organizations have created diagnostic criteria to ease and standardize the diagnostic process, especially in the early stages of the disease. The most widely known criteria come from the UK Parkinson's Disease Society Brain Bank and the U.S. National Institute of Neurological Disorders and Stroke. The PD Society Brain Bank criteria require slowness of movement (bradykinesia) plus either rigidity, resting tremor, or postural instability. Other possible causes for these symptoms need to be ruled out. Finally, three or more of the following features are required during onset or evolution: unilateral onset, tremor at rest, progression in time, asymmetry of motor symptoms, response to levodopa for at least five years, clinical course of at least ten years and appearance of dyskinesias induced by the intake of excessive levodopa. Accuracy of diagnostic criteria evaluated at autopsy is 75-90%, with specialists such as neurologists having the highest rates.

Computed tomography (CT) and magnetic resonance imaging (MM) brain scans of people with PD usually appear normal. These techniques are nevertheless useful to rule out other diseases that can be secondary causes of parkinsonism, such as basal ganglia tumors, vascular pathology and hydrocephalus. A specific technique of MIII, diffusion MIII, has been reported to be useful at discriminating between typical and atypical parkinsonism, although its exact diagnostic value is still under investigation. Dopaminergic function in the basal ganglia can be measured with different PET and SPECT radiotracers. Examples are ioflupane ($^{123}$I) (trade name DATSCAN™) and iometopane (DOPASCAN®) for SPECT or fluorodeoxyglucose ($^{18}$F) for PET. A pattern of reduced dopaminergic activity in the basal ganglia can aid in diagnosing PD.

III. Methods of Assessing Genotypes

A. Assessing for the Presence of SNPs Using Genetic Methods

The methods described herein include determining the identity, e.g., the specific nucleotide, presence or absence, of a SNP associated with HAPH. Samples that are suitable for use in the methods described herein contain genetic material, e.g., genomic DNA (gDNA) or messenger RNA (mRNA). Such nucleic acids are may be extracted from biological samples such as blood, hair, semen (in the case of a bull), mucosal scrapings of the lining of the mouth, and may be extracted from other biological samples including urine or expectorant. The sample itself will typically include nucleated cells or tissue removed from the subject. The subject can be male or female, as well as an adult or young animal. In some embodiments, the sample can be obtained prenatally, either from a fetus or embryo or from the mother (e.g., from fetal or embryonic cells in the maternal circulation). Methods and reagents are known in the art for obtaining, processing, and analyzing samples.

In some cases, a biological sample may be processed for DNA or RNA isolation. For example, DNA or RNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al. (2003). The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAamp® Tissue Kit (Qiagen, Chatsworth, Calif.) and the Wizard® Genomic DNA purification kit (Promega). Non-limiting examples of sources of samples include blood, hair, semen and tissue.

The presence or absence of the SNP can be determined using methods known in the art. For example, gel electrophoresis, capillary electrophoresis, size exclusion chromatography, sequencing, and/or arrays can be used to detect the presence or absence of specific response alleles. Amplification of nucleic acids, where desirable, can be accomplished using methods known in the art, e.g., PCR. In one example, a sample (e.g., a sample comprising genomic DNA), is obtained from a subject. The DNA in the sample is then examined to determine the identity of an allele as described herein, i.e., by determining the identity of one or more alleles associated with a selected response. The identity of an allele can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

Other methods of nucleic acid analysis can include direct manual sequencing (Church and Gilbert, 1988; Sanger et al., 1977; U.S. Pat. No. 5,288,644); automated fluorescent sequencing; single-stranded conformation polymorphism assays (SSCP) (Schafer et al., 1995); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., 1989); denaturing high performance liquid chromatography (DHPLC) (Underhill et al., 1997); infrared matrix-assisted laser desorption/ionization (IR-MALDI) mass spectrometry (WO 99/57318); mobility shift analysis (Orita et al., 1989); restriction enzyme analysis (Flavell et al., 1978; Geever et al., 1981); quantitative real-time PCR (Raca et al., 2004); heteroduplex analysis; chemical mismatch cleavage (CMC) (Cotton et al., 1985); RNase protection assays (Myers et al., 1985); use of polypeptides that recognize nucleotide mismatches, e.g., *E. coli* mutS protein; allele-specific PCR, and combinations of such methods. See, e.g., U.S. Patent Publication No. 2004/0014095, which is incorporated herein by reference in its entirety.

Sequence analysis can also be used to detect specific polymorphic variants. For example, polymorphic variants can be detected by sequencing exons, introns, 5' untranslated sequences, or 3' untranslated sequences. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined. Real-time pyrophosphate DNA sequencing is yet another approach to detection of polymorphisms and polymorphic variants (Alderborn et al., 2000). Additional methods include, for example, PCR amplification in combination with denaturing high performance liquid chromatography (dHPLC) (Underhill et al., 1997).

PCR® refers to procedures in which target nucleic acid (e.g., genomic DNA) is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. See e.g., *PCR Primer: A Laboratory Manual*, Dieffenbach and Dveksler, (Eds.); McPherson et al., 2000; Mattila et al., 1991; Eckert et al., 1991; PCR (eds. McPherson et al., IRL Press, Oxford); and U.S. Pat. No. 4,683,202. Other amplification methods that may be employed include the ligase chain reaction (LCR) (Wu and Wallace, 1989; Landegren et al., 1988), transcription amplification (Kwoh et al., 1989), self-sustained sequence replication (Guatelli et al., 1990), and nucleic acid based sequence amplification (NASBA). Guidelines for selecting primers for PCR amplification are well known in the art. See, e.g., McPherson et al. (2000). A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In some cases, PCR conditions and primers can be developed that amplify a product only when the variant allele is present or only when the wild type allele is present (MSPCR or allele-specific PCR). For example, patient DNA and a control can be amplified separately using either a wild-type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., 1994). The PNA probe can be designed to specifically hybridize to a nucleic acid comprising a polymorphic variant.

In some cases, allele-specific oligonucleotides can also be used to detect the presence of a polymorphic variant. For example, polymorphic variants can be detected by performing allele-specific hybridization or allele-specific restriction digests. Allele specific hybridization is an example of a method that can be used to detect sequence variants, including complete genotypes of a subject (e.g., a mammal such as a human). See Stoneking et al., 1991; Prince et al., 2001. An "allele-specific oligonucleotide" (also referred to herein as an "allele-specific oligonucleotide probe") is an oligonucleotide that is specific for particular a polymorphism can be prepared using standard methods (see, Ausubel et al., 2003). Allele-specific oligonucleotide probes typically can be approximately 10-50 base pairs, preferably approximately 15-30 base pairs, that specifically hybridizes to a nucleic acid region that contains a polymorphism. Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. In some cases, dot-blot hybridization of amplified oligonucleotides with allele-specific oligonucleotide (ASO) probes can be performed. See, for example, Saiki et al. (1986).

In some embodiments, allele-specific restriction digest analysis can be used to detect the existence of a polymorphic variant of a polymorphism, if alternate polymorphic variants of the polymorphism result in the creation or elimination of a restriction site. Allele-specific restriction digests can be performed in the following manner. A sample containing genomic DNA is obtained from the individual and genomic DNA is isolated for analysis. For nucleotide sequence variants that introduce a restriction site, restriction digest with the particular restriction enzyme can differentiate the alleles. In some cases, polymerase chain reaction (PCR) can be used to amplify a region comprising the polymorphic site, and restriction fragment length polymorphism analysis is conducted (see, Ausubel et al., 2003). The digestion pattern of the relevant DNA fragment indicates the presence or absence of a particular polymorphic variant of the polymorphism and is therefore indicative of the subject's response allele. For sequence variants that do not alter a common restriction site, mutagenic primers can be designed that introduce a restriction site when the variant allele is present or when the wild type allele is present. For example, a portion of a nucleic acid can be amplified using the mutagenic primer and a wild type primer, followed by digest with the appropriate restriction endonuclease.

In some embodiments, fluorescence polarization template-directed dye-terminator incorporation (FP-TDI) is used to determine which of multiple polymorphic variants of a polymorphism is present in a subject (Chen et al., 1999). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

In some cases, DNA containing an amplified portion may be dot-blotted, using standard methods (see Ausubel et al., 2003), and the blot contacted with the oligonucleotide probe. The presence of specific hybridization of the probe to the DNA is then detected. Specific hybridization of an allele-specific oligonucleotide probe (specific for a polymorphic variant indicative of a predicted response to a method of treating an SSD) to DNA from the subject is indicative of a subject's response allele.

The methods can include determining the genotype of a subject with respect to both copies of the polymorphic site present in the genome (i.e., both alleles). For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

Methods of nucleic acid analysis to detect polymorphisms and/or polymorphic variants can include, e.g., microarray analysis. Hybridization methods, such as Southern analysis, Northern analysis, or in situ hybridizations, can also be used (see, Ausubel et al., 2003). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to the methods provided herein.

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70% (e.g., 80%, 90%, 95%, 98% or more) identity to the target sequence. The probe sequence must also be sufficiently long so that the probe exhibits selectivity for the target sequence over non-target sequences. For example, the probe will be at least 20 (e.g., 25, 30, 35, 50, 100, 200, 300, 400, 500, 600, 700, 800, 900 or more) nucleotides in length. In some embodiments, the probes are not more than 30, 50, 100, 200, 300, 500, 750, or 1000 nucleotides in length. Probes are typically about 20 to about $1 \times 10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

The probe can be a test probe such as a probe that can be used to detect polymorphisms in a region described herein (e.g., an allele associated with treatment response as described herein). In some embodiments, the probe can bind to another marker sequence associated with SZ, SPD, or SD as described herein or known in the art.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially such from Applied Biosystems, e.g., the Assays-on-Demand SNP kits Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson (1998); Wheeless et al. (1994); U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), TEXAS RED™ (Molecular Probes, Inc., Eugene, Oreg.), 5-(and -6)-carboxy-X-rhodamine, lissamine rhodamine B, 5-(and -6)-carboxyfluorescein, fluorescein-5-isothiocyanate (FITC), 7-diethylaminocoumarin-3-carboxylic acid, tetramethylrhodamine-5-(and -6)-isothiocyanate, 5-(and -6)-carboxytetramethylrhodamine, 7-hydroxycoumarin-3-carboxylic acid, 6-[fluorescein 5-(and -6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and CASCADE™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^{3}H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

In particular, commercial kits and assays are known for detecting rs6265 (Sheikh et al. *Psychiatr Genet.* 20(3):109-12, 2010; Sánchez-Romero et al., *Pharmacogenomics* 10(6): 989-95, 2009) which are incorporated herein by reference.

B. Markers in Linkage Disequilibrium (LD)

Linkage disequilibrium (LD) is a measure of the degree of association between alleles in a population. One of skill in the art will appreciate that alleles involving markers in LD with the polymorphisms described herein can also be used in a similar manner to those described herein. Methods of calculating LD are known in the art (see, e.g., Morton et al., 2001; Tapper et al., 2005; Maniatis et al., 2002). Thus, in some cases, the methods can include analysis of polymorphisms that are in LD with a polymorphism described herein. Methods are known in the art for identifying such polymorphisms; for example, the International HapMap Project provides a public database that can be used, see hapmap.org, as well as The International HapMap Consortium (2003) and The International HapMap Consortium (2005). Generally, it will be desirable to use a HapMap constructed using data from individuals who share ethnicity with the subject. For example, a HapMap for Caucasians would ideally be used to identify markers in LD with an exemplary marker described herein for use in genotyping a subject of Caucasian descent.

Alternatively, methods described herein can include analysis of polymorphisms that show a correlation coefficient ($r^2$) of value >0.5 with the markers described herein. Results can be obtained from on line public resources such as HapMap.org on the World Wide Web. The correlation coefficient is a measure of LD, and reflects the degree to which alleles at two loci (for example, two SNPs) occur together, such that an allele at one SNP position can predict the correlated allele at a second SNP position, in the case where $r^2$ is >0.5.

C. Protein Based Methods

1. Immunoassays

Thus, in accordance with the present disclosure, methods are provided for determining protein sequence. There are a variety of methods that can be used to assess protein structure. One such approach is to perform protein identification with the use of antibodies. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antibody" also refers to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art.

Means for preparing and characterizing antibodies, both polyclonal and monoclonal, are also well known in the art (see, e.g., Antibodies: A Laboratory Manual, Cold Spring Harbor Laboratory, 1988; incorporated herein by reference). In particular, antibodies to calcyclin, calpactin I light chain, astrocytic phosphoprotein PEA-15 and tubulin-specific chaperone A are contemplated.

In accordance with the present invention, immunodetection methods are provided. Some immunodetection methods include enzyme linked immunosorbent assay (ELISA), radioimmunoassay (MA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle & Ben-Zeev O, 1999; Gulbis & Galand, 1993; De Jager et al., 1993; and Nakamura et al., 1987, each incorporated herein by reference.

In general, the immunobinding methods include obtaining a sample suspected of containing a relevant polypeptide, and contacting the sample with a first antibody under conditions effective to allow the formation of immunocomplexes. In terms of antigen detection, the biological sample analyzed may be any sample that is suspected of containing an antigen, such as, for example, a tissue section or specimen, a homogenized tissue extract, a cell, or even a biological fluid.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays are in essence binding assays. Certain immunoassays are the various types of enzyme linked immunosorbent assays (ELISAs) and radioimmunoassays (MA) known in the art. However, it will be readily appreciated that detection is not limited to such techniques, and Western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the antigen, such as a clinical sample, is added to the wells. After binding and washing to remove non-specifically bound immune complexes, the bound antigen may be detected. Detection is generally achieved by the addition of another antibody that is linked to a detectable label. This type of ELISA is a simple sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and then contacted with the anti-ORF message and anti-ORF translated product antibodies of the invention. After binding and washing to remove non-specifically bound immune complexes, the bound anti-ORF message and anti-ORF translated product antibodies are detected. Where the initial anti-ORF message and anti-ORF translated product antibodies are linked to a detectable label, the immune complexes may be detected directly. Again, the immune complexes may be detected using a second antibody that has binding affinity for the first anti-ORF message and anti-ORF translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background. The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Also contemplated in the present invention is the use of immunohistochemistry. This approach uses antibodies to detect and quantify antigens in intact tissue samples. Generally, frozen-sections are prepared by rehydrating frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and cutting up to 50 serial permanent sections.

2. Mass Spectrometry

By exploiting the intrinsic properties of mass and charge, mass spectrometry (MS) can resolved and confidently identified a wide variety of complex compounds, including proteins. Traditional quantitative MS has used electrospray ionization (ESI) followed by tandem MS (MS/MS) (Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can generate mass spectrometry profiles that identify variation in residues 66 of brain derived neurotrophic factor.

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 .mu.L/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer, is delivered to tip through an internal passage from a suitable source (such as from a chromatograph or directly from a sample solution via a liquid flow controller). By applying pressure to the sample in the capillary, the liquid leaves the capillary tip as small highly electrically charged droplets and further undergoes desolvation and breakdown to form single or multicharged gas phase ions in the form of an ion beam. The ions are then collected by the grounded (or negatively charged) interface plate and led through the orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; and 5,986,258.

In ESI tandem mass spectroscopy (ESI/S/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances sample clean-up is required (Nelson et al., 1994; Gobom et al., 2000).

Secondary ion mass spectroscopy, or SIMS, is an analytical method that uses ionized particles emitted from a surface for mass spectroscopy at a sensitivity of detection of a few parts per billion. The sample, surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analysis by the mass spectrometer in this method.

Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and the separation of fragments, are due to different size causing different velocity. Each ion mass will thus have a different flight-time to the detector.

One can either form positive ions or negative ions for analysis. Positive ions are made from regular direct photoionization, but negative ion formation requires a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectrum.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Li et al., 2000; Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multi-component quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

D. Application of Results

Described herein are a variety of methods for predicting a Parkinson's disease patient's response to optimized drug therapy and/or deep brain stimulation based on the presence or absence of an allele defined by the SNPs designated rs6265, which results in a Val→Met substitution at residue 66 of brain derived neurotrophic factor. As used herein, "determining the identity of an allele" includes obtaining information regarding the identity (i.e., of a specific nucleotide), presence or absence of one or more specific SNP alleles in a subject. Determining the identity of an allele can, but need not, include obtaining a sample comprising DNA, RNA or protein from a subject, and/or assessing the identity, presence or absence of one or more markers in the sample. The individual or organization who determines the identity of the allele need not actually carry out the physical analysis of a sample from a subject; the methods can include using information obtained by analysis of the sample by a third party. Thus, the methods can include steps that occur at more than one site. For example, a sample can be obtained from a subject at a first site, such as a hospital or doctor's office. The sample can be analyzed at the same or a second site, e.g., at a laboratory or other testing facility.

Determining the identity of an allele can also include or consist of reviewing a subject's medical history, where the medical history includes information regarding the identity, presence or absence of one or more response alleles in the subject, e.g., results of a genetic test.

In some embodiments, to determine the identity of an allele described herein, a biological sample that includes nucleated cells (such as blood, hair, semen, a cheek swab or mouthwash) is prepared and analyzed for the presence or absence of preselected markers. Such diagnoses may be performed by diagnostic laboratories, or, alternatively, diagnostic kits can be manufactured sold commercially.

Results of these tests, and optionally interpretive information, can be returned to the patient, doctor or healthcare institution subject or other third party. The results can be used in a number of ways. The information can be, e.g., communicated to the patient or doctor so as to initiate, alter or guide therapeutic intervention, e.g., with a prognosis and optionally interpretive materials that help the subject understand the test results and prognosis. The information may also simply indicate that the subject should be assigned to a specific category, e.g., as a long-term responder to ODT or not. The presence or absence of the allele in a patient may be ascertained by using any of the methods described herein.

IV. Parkinson's Therapies

There is no cure for Parkinson's disease, but medications, surgery and multidisciplinary management can provide relief from the symptoms. The main families of drugs useful for treating motor symptoms are levodopa (usually combined with a dopa decarboxylase inhibitor or COMT inhibitor), dopamine agonists and MAO-B inhibitors. The stage of the disease determines which group is most useful. Two stages are usually distinguished: an initial stage in which the individual with PD has already developed some disability for which he needs pharmacological treatment, then a second stage in which an individual develops motor complications related to levodopa usage. Treatment in the initial stage aims for an optimal tradeoff between good symptom control and side-effects resulting from improvement of dopaminergic function. The start of levodopa (or L-DOPA) treatment may be delayed by using other medications such as MAO-B inhibitors and dopamine agonists, in the hope of delaying the onset of dyskinesias. In the second stage the aim is to reduce symptoms while controlling fluctuations of the response to medication. Sudden withdrawals from medication or overuse have to be managed. When medications are not enough to control symptoms, surgery and deep brain stimulation can be of use. In the final stages of the disease, palliative care is provided to improve quality of life.

A. Levodopa

Levodopa has been the most widely used treatment for over 30 years. L-DOPA is converted into dopamine in the dopaminergic neurons by dopa decarboxylase. Since motor symptoms are produced by a lack of dopamine in the substantia nigra, the administration of L-DOPA temporarily diminishes the motor symptoms.

Only 5-10% of L-DOPA crosses the blood-brain barrier. The remainder is often metabolized to dopamine elsewhere, causing a variety of side effects including nausea, dyskinesias and joint stiffness. Carbidopa and benserazide are peripheral dopa decarboxylase inhibitors, which help to prevent the metabolism of L-DOPA before it reaches the dopaminergic neurons, therefore reducing side effects and increasing bioavailability. They are generally given as combination preparations with levodopa. Existing preparations are carbidopa/levodopa (co-careldopa) and benserazide/levodopa (co-beneldopa). Levodopa has been related to dopamine dysregulation syndrome, which is a compulsive overuse of the medication, and punding. There are controlled release versions of levodopa in the form intravenous and intestinal infusions that spread out the effect of the medication. These slow-release levodopa preparations have not shown an increased control of motor symptoms or motor complications when compared to immediate release preparations.

Tolcapone inhibits the COMT enzyme, which degrades dopamine, thereby prolonging the effects of levodopa. It has been used to complement levodopa; however, its usefulness is limited by possible side effects such as liver damage. A similarly effective drug, entacapone, has not been shown to cause significant alterations of liver function. Licensed preparations of entacapone contain entacapone alone or in combination with carbidopa and levodopa.

Levodopa preparations lead in the long term to the development of motor complications characterized by involuntary movements called dyskinesias and fluctuations in the response to medication. When this occurs a person with PD can change from phases with good response to medication and few symptoms ("on" state), to phases with no response to medication and significant motor symptoms ("off" state). For this reason, levodopa doses are kept as low as possible while maintaining functionality. Delaying the initiation of therapy with levodopa by using alternatives (dopamine agonists and MAO-B inhibitors) is common practice. A former strategy to reduce motor complications was to withdraw L-DOPA medication for some time. This is discouraged now, since it can bring dangerous side effects such as neuroleptic malignant syndrome. Most people with PD will eventually need levodopa and later develop motor side effects.

B. Dopamine Agonists

Several dopamine agonists that bind to dopaminergic post-synaptic receptors in the brain have similar effects to levodopa. These were initially used for individuals experiencing on-off fluctuations and dyskinesias as a complementary therapy to levodopa; they are now mainly used on their own as an initial therapy for motor symptoms with the aim of delaying motor complications. When used in late PD they are useful at reducing the off periods. Dopamine agonists include bromocriptine, pergolide, pramipexole, ropinirole, piribedil, cabergoline, apomorphine and lisuride.

Dopamine agonists produce significant, although usually mild, side effects including drowsiness, hallucinations, insomnia, nausea and constipation. Sometimes side effects appear even at a minimal clinically effective dose, leading the physician to search for a different drug. Compared with levodopa, dopamine agonists may delay motor complications of medication use but are less effective at controlling symptoms. Nevertheless, they are usually effective enough to manage symptoms in the initial years. They tend to be more expensive than levodopa. Dyskinesias due to dopamine agonists are rare in younger people who have PD, but along with other side effects, become more common with age at onset. Thus dopamine agonists are the preferred initial treatment for earlier onset, as opposed to levodopa in later onset. Agonists have been related to impulse control disorders (such as compulsive sexual activity and eating, and pathological gambling and shopping) even more strongly than levodopa.

Apomorphine, a non-orally administered dopamine agonist, may be used to reduce off periods and dyskinesia in late PD. It is administered by intermittent injections or continuous subcutaneous infusions. Since secondary effects such as confusion and hallucinations are common, individuals receiving apomorphine treatment should be closely monitored. Two dopamine agonists that are administered through skin patches (lisuride and rotigotine) and are useful for people in the initial stages and possibly in the control of off states in those in the advanced state.

C. MAO-B Inhibitors

MAO-B inhibitors (selegiline and rasagiline) increase the level of dopamine in the basal ganglia by blocking its metabolism. They inhibit monoamine oxidase B (MAO-B) which breaks down dopamine secreted by the dopaminergic neurons. The reduction in MAO-B activity results in increased L-DOPA in the striatum. Like dopamine agonists, MAO-B inhibitors used as monotherapy improve motor symptoms and delay the need for levodopa in early disease, but produce more adverse effects and are less effective than levodopa. There are few studies of their effectiveness in the advanced stage, although results suggest that they are useful to reduce fluctuations between on and off periods. An initial study indicated that selegiline in combination with levodopa increased the risk of death, but this was later disproven.

D. Other Drugs

Other drugs such as amantadine and anti-cholinergics may be useful as treatment of motor symptoms. However, the evidence supporting them lacks quality, so they are not first choice treatments. In addition to motor symptoms, PD is accompanied by a diverse range of symptoms. A number of drugs have been used to treat some of these problems.[53] Examples are the use of quetiapine for psychosis, cholinesterase inhibitors for dementia, and modafinil for daytime sleepiness. A 2010 meta-analysis found that non-steroidal anti-inflammatory drugs (apart from paracetamol and aspirin), have been associated with at least a 15% (higher in long-term and regular users) reduction of incidence of the development of Parkinson's disease.

E. Surgery

Treating motor symptoms with surgery was once a common practice, but since the discovery of levodopa, the number of operations declined. Studies in the past few decades have led to great improvements in surgical techniques, so that surgery is again being used in people with advanced PD for whom drug therapy is no longer sufficient. Surgery for PD can be divided in two main groups: lesional and deep brain stimulation (DBS). Target areas for DBS or lesions include the thalamus, the globus pallidus or the subthalamic nucleus. Deep brain stimulation (DBS) is the most commonly used surgical treatment, developed in the 1980s by Alim-Louis Benabid and others. It involves the implantation of a medical device called a brain pacemaker, which sends electrical impulses to specific parts of the brain. DBS is recommended for people who have PD with motor fluctuations and tremor inadequately controlled by medication, or to those who are intolerant to medication, as long as they do not have severe neuropsychiatric problems. Other, less common, surgical therapies involve intentional formation of lesions to suppress overactivity of specific subcortical areas. For example, pallidotomy involves surgical destruction of the globus pallidus to control dyskinesia.

F. Rehabilitation

There is some evidence that speech or mobility problems can improve with rehabilitation, although studies are scarce and of low quality. Regular physical exercise with or without physiotherapy can be beneficial to maintain and improve mobility, flexibility, strength, gait speed, and quality of life. However, when an exercise program is performed under the supervision of a physiotherapist, there are more improvements in motor symptoms, mental and emotional functions, daily living activities, and quality of life compared to a self-supervised exercise program at home. In terms of improving flexibility and range of motion for people experiencing rigidity, generalized relaxation techniques such as gentle rocking have been found to decrease excessive muscle tension. Other effective techniques to promote relaxation include slow rotational movements of the extremities and trunk, rhythmic initiation, diaphragmatic breathing, and meditation techniques. As for gait and addressing the challenges associated with the disease such as hypokinesia (slowness of movement), shuffling and decreased arm swing; physiotherapists have a variety of strategies to improve functional mobility and safety. Areas of interest with respect to gait during rehabilitation programs focus on but are not limited to improving gait speed, base of support, stride length, trunk and arm swing movement. Strategies include utilizing assistive equipment (pole walking and treadmill walking), verbal cueing (manual, visual and auditory), exercises (marching and PNF patterns) and altering environments (surfaces, inputs, open vs. closed). Strengthening exercises have shown improvements in strength and motor function for people with primary muscular weakness and weakness related to inactivity with mild to moderate Parkinson's disease. However, reports show a significant interaction between strength and the time the medications was taken. Therefore, it is recommended that people with PD should perform exercises 45 minutes to one hour after medications, when they are at their best. Also, due to the forward flexed posture, and respiratory dysfunctions in advanced Parkinson's disease, deep diaphragmatic breathing exercises are beneficial in improving chest wall mobility and vital capacity. Exercise may improve constipation.

One of the most widely practiced treatments for speech disorders associated with Parkinson's disease is the Lee Silverman voice treatment (LSVT). Speech therapy and specifically LSVT may improve speech. Occupational therapy (OT) aims to promote health and quality of life by helping people with the disease to participate in as many of their daily living activities as possible. There have been few studies on the effectiveness of OT and their quality is poor, although there is some indication that it may improve motor skills and quality of life for the duration of the therapy.

G. Palliative Care

Palliative care is specialized medical care for people with serious illnesses, including Parkinson's disease. The goal of this speciality is to improve quality of life for both the person suffering from Parkinson's disease and the family by providing relief from the symptoms, pain, and stress of illnesses. As Parkinson's is not a curable disease, all treatments are focused on slowing decline and improving quality of life, and are therefore palliative in nature.

Palliative care should be involved earlier, rather than later in the disease course. Palliative care specialists can help with physical symptoms, emotional factors such as loss of function and jobs, depression, fear, and existential concerns.

Along with offering emotional support to both the patient and family, palliative care serves an important role in addressing goals of care. People with Parkinson's disease may have many difficult decisions to make as th disease progresses such as wishes for feeding tube, non-invasive ventilator, and tracheostomy; wishes for or against cardio-pulmonary resuscitation; and when to use hospice care. Palliative care team members can help answer questions and guide people with Parkinson's disease on these complex and emotional topics to help them make the best decision based on their own values.

H. Other Treatments

Muscles and nerves that control the digestive process may be affected by PD, resulting in constipation and gastroparesis (food remaining in the stomach for a longer period of time than normal). A balanced diet, based on periodical nutritional assessments, is recommended and should be designed to avoid weight loss or gain and minimize consequences of gastrointestinal dysfunction. As the disease advances, swallowing difficulties (dysphagia) may appear. In such cases it may be helpful to use thickening agents for liquid intake and an upright posture when eating, both measures reducing the risk of choking. Gastrostomy to deliver food directly into the stomach is possible in severe cases.

Levodopa and proteins use the same transportation system in the intestine and the blood-brain barrier, thereby competing for access. When they are taken together, this results in a reduced effectiveness of the drug. Therefore, when levodopa is introduced, excessive protein consumption is discouraged and well balanced Mediterranean diet is recommended. In advanced stages, additional intake of low-protein products such as bread or pasta is recommended for similar reasons. To minimize interaction with proteins, levodopa should be taken 30 minutes before meals. At the same time, regimens for PD restrict proteins during breakfast and lunch, allowing protein intake in the evening.

Repetitive transcranial magnetic stimulation temporarily improves levodopa-induced dyskinesias. Its usefulness in PD is an open research topic, although recent studies have shown no effect by rTMS. Several nutrients have been proposed as possible treatments; however there is no evidence that vitamins or food additives improve symptoms. There is no evidence to substantiate that acupuncture and practice of Qigong, or T'ai chi, have any effect on the course of the disease or symptoms. Further research on the viability of Tai chi for balance or motor skills are necessary. Fava beans and velvet beans are natural sources of levodopa and are eaten by many people with PD. While they have shown some effectiveness in clinical trials, their intake is not free of risks. Life-threatening adverse reactions have been described, such as the neuroleptic malignant syndrome.

I. Deep Brain Stimulation

Deep brain stimulation (DBS) is a neurosurgical procedure involving the implantation of a medical device called a brain pacemaker, which sends electrical impulses, through implanted electrodes, to specific parts of the brain (brain nucleus) for the treatment of movement and affective disorders. DBS in select brain regions has provided therapeutic benefits for otherwise-treatment-resistant movement and affective disorders such as Parkinson's disease, essential tremor, dystonia, chronic pain, major depression and obsessive-compulsive disorder (OCD). Despite the long history of DBS, its underlying principles and mechanisms are still not clear. DBS directly changes brain activity in a controlled manner, its effects are reversible (unlike those of lesioning techniques), and it is one of only a few neurosurgical methods that allow blinded studies.

The Food and Drug Administration (FDA) approved DBS as a treatment for essential tremor in 1997, for Parkinson's disease in 2002, dystonia in 2003, and OCD in 2009. DBS is also used in research studies to treat chronic pain and has been used to treat various affective disorders, including major depression; neither of these applications of DBS have yet been FDA-approved. While DBS has proven helpful for some patients, there is potential for serious complications and side effects.

The deep brain stimulation system consists of three components: the implanted pulse generator (IPG), the lead, and the extension. The IPG is a battery-powered neurostimulator encased in a titanium housing, which sends electrical pulses to the brain to interfere with neural activity at the target site. The lead is a coiled wire insulated in polyurethane with four platinum iridium electrodes and is placed in one or two different nuclei of the brain. The lead is connected to the IPG by the extension, an insulated wire that runs below the skin, from the head, down the side of the neck, behind the ear to the IPG, which is placed subcutaneously below the clavicle or, in some cases, the abdomen. The IPG can be calibrated by a neurologist, nurse, or trained technician to optimize symptom suppression and control side-effects.

DBS leads are placed in the brain according to the type of symptoms to be addressed. For non-parkinsonian essential tremor, the lead is placed in the ventrointermediate nucleus (VIM) of the thalamus; for dystonia and symptoms associated with Parkinson's disease (rigidity, bradykinesia/akinesia, and tremor), the lead may be placed in either the globus pallidus internus or the subthalamic nucleus; for OCD and Depression to the nucleus Accumbens; for incessant pain to the posterior thalamic region or periaqueductal gray; for Parkinson's plus patients to two nuclei simultaneously, subthalamic nucleus and tegmental nucleus of pons, with the use of two pulse generators; and for epilepsy treatment to the anterion thalamic nucleus.

All three components are surgically implanted inside the body. Lead implantation may take place under local anesthesia or with the patient under general anesthesia ("asleep DBS") such as for dystonia. A hole about 14 mm in diameter is drilled in the skull and the probe electrode is inserted stereotactically. During the awake procedure with local anesthesia, feedback from the patient is used to determine optimal placement of the permanent electrode. During the asleep procedure, intraoperative MM guidance is used for direct visualization of brain tissue and device. The installation of the IPG and extension leads occurs under general anesthesia. The right side of the brain is stimulated to address symptoms on the left side of the body and vice versa.

DBS does not cure Parkinson's disease, but it can help manage some of its symptoms and subsequently improve the patient's quality of life. At present, the procedure is used only for patients whose symptoms cannot be adequately controlled with medications, or whose medications have severe side-effects. Its direct effect on the physiology of brain cells and neurotransmitters is currently debated, but by sending high frequency electrical impulses into specific areas of the brain it can mitigate symptoms and/or directly diminish the side-effects induced by parkinsonian medications, allowing a decrease in medications, or making a medication regimen more tolerable.

There are a few sites in the brain that can be targeted to achieve differing results, so each patient must be assessed individually, and a site will be chosen based on their needs. Traditionally, the two most common sites are the subthalamic nucleus (STN) and the globus pallidus interna (GPi), but other sites, such as the caudal zona incerta and the pallidofugal fibers medial to the STN, are being evaluated and showing promise.

DBS is approved in the United States by the Food and Drug Administration for the treatment of Parkinson's disease. DBS carries the risks of major surgery, with a complication rate related to the experience of the surgical team. The major complications include hemorrhage (1-2%) and infection (3-5%).

V. Articles of Manufacture

Also provided herein are articles of manufacture comprising probes that hybridize to or prime near the region of chromosome containing the SNP described herein. For example, any of the probes for detecting the SNP described herein can be combined with packaging material to generate articles of manufacture or kits. The kit can include one or more other elements including: instructions for use; and other reagents such as a label or an agent useful for attaching a label to the probe. Instructions for use can include instructions for a method described herein. Other instructions can include instructions for attaching a label to the probe, instructions for performing analysis with the probe, and/or instructions for obtaining a sample to be analyzed from a subject. In some cases, the kit can include a labeled probe that hybridizes to a region of human chromosome as described herein.

The kit can also include one or more additional reference or control probes that hybridize to the same chromosome or another chromosome or portion thereof. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes. Kits for use in self-testing can also be provided. Such test kits can include devices and instructions that a subject can use to obtain a biological sample (e.g., buccal cells, blood) without the aid of a health care provider. For example, buccal cells can be obtained using a buccal swab or brush, or using mouthwash.

Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the sample can be coded, for example, with a bar code for identifying the subject who provided the sample.

VI. Databases and Reports

Also provided herein are databases that include medical information including the genetic make-up of a subject. The list is stored, e.g., on a flat file or computer-readable medium. The databases can further include information regarding one or more subjects, e.g., whether a subject is affected or unaffected, clinical information such as endophenotype, age of onset of symptoms, any treatments administered and outcomes (e.g., data relevant to pharmacogenomics, diagnostics or theranostics), and other details, e.g., about the disorder in the subject, or environmental or other genetic factors. The databases can be used to detect correlations between a particular allele or genotype and the information regarding the subject.

The methods described herein can also include the generation of reports, e.g., for use by a subject, care giver, payor, or researcher, that include information regarding a subject's response allele(s), and optionally further information such as treatments administered, treatment history, medical history, predicted response, and actual response. The reports can be recorded in a tangible medium, e.g., a computer-readable disk, a solid state memory device, or an optical storage device.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Subjects and Methods

Subjects.

The inventors genotyped subjects enrolled in the Vanderbilt DBS in Early Stage PD clinical trial (Clinical Trials.gov NCT00282152) (Charles et al., 2014). The study was approved by the U.S. Food and Drug Administration (IDE #G050016) and the Vanderbilt Institutional Review Board (IRB #040797). The study population consisted of twenty-nine, early-stage PD subjects prospectively treated for two years with bilateral STN DBS plus medication ("DBS") or optimized drug therapy (ODT). Twenty-eight subjects (15 DBS, 13 ODT) provided written consent for genetic analysis. Subjects were age 50-75 years, diagnosed with idiopathic PD, Hoehn and Yahr Stage II when off medication, treated with antiparkinsonian medications for >6 months but ≤4 years and with no history of dyskinesia or other motor fluctuations (Table 1).

Treatments.

All subjects randomized to DBS were implanted bilaterally with leads in the STN using standard-of-care methodology for Vanderbilt University Medical Center as described previously (Charles et al., 2014). Stimulation was optimized throughout the trial to maximize clinical benefit while minimizing adverse effects. In order to reduce investigator bias, medication optimization for both treatment groups was performed by each subject's original treating neurologist.

Clinical Metrics.

Subjects were followed for 24 months. Assessments included UPDRS at baseline and six-month intervals and the Parkinson's Disease Questionnaire-39 (PDQ-39, patient reported, quality-of-life measures) at baseline and twelve-month intervals. UPDRS-III (excluding rigidity) was videotaped in the ON therapy states, and videos were scored by an independent, blinded PD expert certified in scoring the UPDRS (Charles et al., 2014). Levodopa-equivalent daily doses (LEDDs) were calculated as described previously (Charles et al., 2014).

Genotyping.

Bdnf rs6265 genotyping was performed on subject blood or saliva samples using the 59 exonuclease allelic discrimination Taqman assay. High-quality genomic DNA was isolated using the prepIT-L2P (DNA Genotek) reagent. SNP assays were performed with 20 ng of genomic DNA in triplicate using Taqman Genotyping mastermix (Applied Biosystems, #4371353) and a pre-designed rs6265 SNP Genotyping Assay (Applied Biosystems, Assay ID: C_11592758_10). Reactions were run in a Real-Time PCR instrument (Life Technologies, ViiA 7) using the Genotyping Program.

Statistical Analysis.

Figure 2:
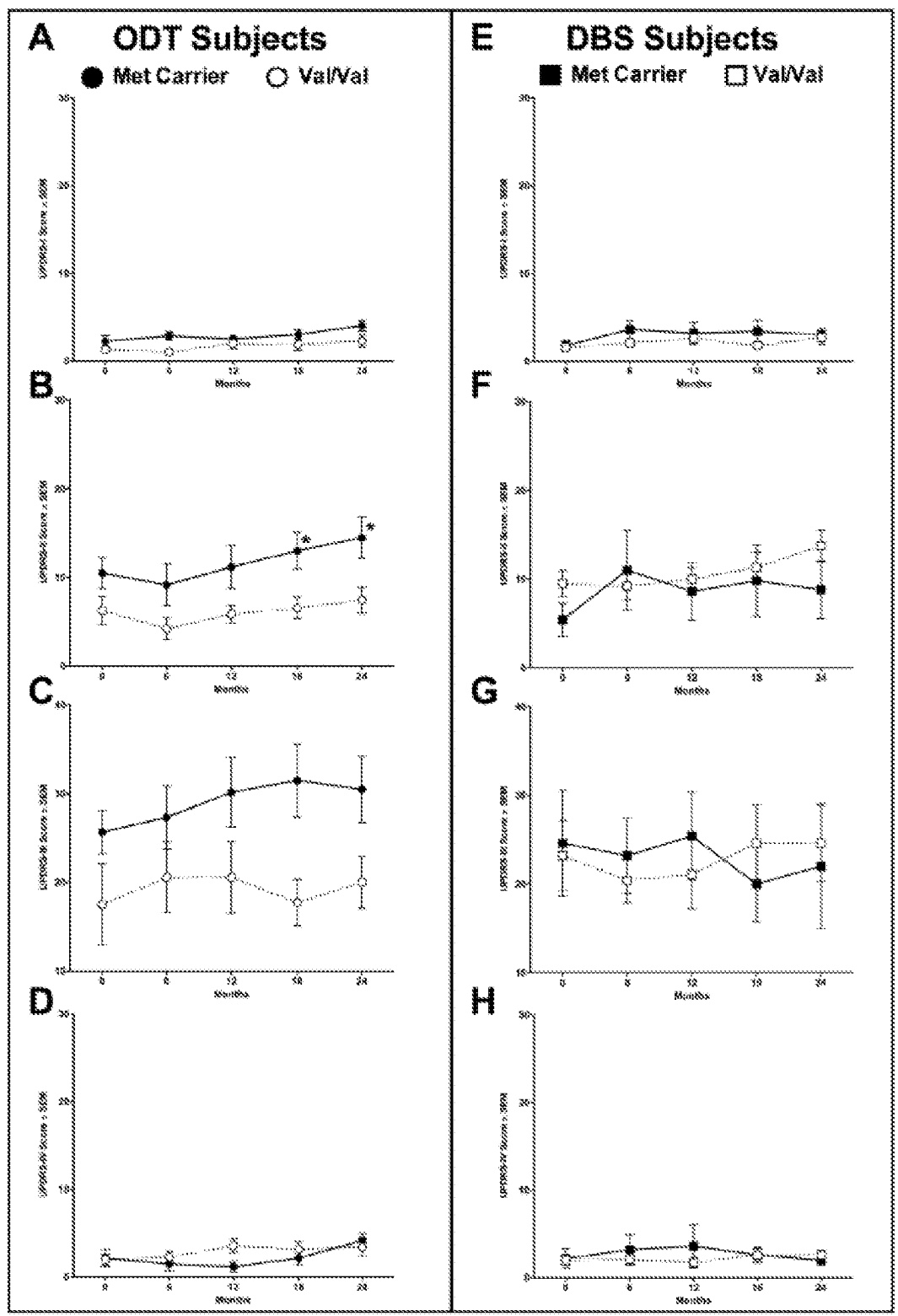
FIGS. 2A-H. Impact of Bdnf variant rs6265 on UPDRS parts I-IV over 24 Months. UPDRS-II. Met allele carriers in the ODT arm displayed significantly higher (worse) scores at 24 months compared to Val/Val subjects (FIG. 2B, *, p=0.017). UPDRS parts I, III and IV. No significant differences were observed due to either Bdnf rs6265 status or treatment (FIG. 2A, FIGS. 2C-H, p>0.05). Values represent the mean±SEM.

The inventors compared the outcomes of DBS and ODT patients with and without Met alleles (i.e., Val/Met and Met/Met vs. Val/Val) using a mixed effects model that included the fixed effects (genotype, treatment, time) as well as their pairwise and three-way interactions and an autoregressive covariance structure to account for repeated measures at baseline, 12 and 24 months. Parameters were estimated from this model and used to compare group differences in terms of average scores at baseline to 6, 12, 18 and 24 months. Statistical significance was set at $p<0.05$. All tests were two-tailed. These analyses were performed using the statistical software SAS (version 9.3; SAS Institute, Cary, N.C.) and R (world-wide-web at r-project.org/). Of special note, although the sample size is constrained due to the nature of the condition and treatment, the inventors estimated 80% statistical power to detect a change of ±18.2 points in the 24-month UPDRS between genotypes, a clinically meaningful change (Shulman et al., 2010). This calculation is based on an alpha of 0.05, SD of 10.6 and the numbers in each group n=6 (Met allele carriers) and n=7 (Val/Val subjects) using a Student's t-test, and it was performed using the PS program (version 3.0) (Dupont et al., 1998).

of the Met allele in the ODT arm was associated with higher scores in all of the UPDRS subscores (FIGS. 2A-D), with significantly higher (≈7 points) UPDRS-II scores at 18 (p=0.03) and 24 months (14.50±2.32, p=0.017, FIG. 2B). In contrast, no significant differences due to genotype were observed between Met allele carriers and Val/Val subjects receiving DBS at any time point with any clinical metric (FIGS. 1C-D, FIGS. 2E-H, p>0.05).

Comparisons were also made between treatments within subjects of identical genotype. At 24 months, Met allele carriers treated with DBS displayed lower UPDRS scores (≈17 points less) compared to Met allele carriers treated with

| Baseline Characteristics | All Val/Val (n = 17) | All Met Carriers (n = 11) | DBS Val/Val (n = 10) | DBS Met (n = 5) | ODT Val/Val (n = 7) | ODT Met (n = 6) |
|---|---|---|---|---|---|---|
| Gender | | | | | | |
| Men | 14 | 11 | 9 | 5 | 5 | 6 |
| Women | 3 | 0 | 1 | 0 | 2 | 0 |
| Age (years) at enrollment | | | | | | |
| Mean | 61.2 (1.8) | 59.7 (1.5) | 60.4 (2.4) | 61.1 (1.9) | 62.2 (2.8) | 58.5 (2.4) |
| Range | 52.2-78.9 | 50.2-67.9 | 52.2-73.9 | 55.4-67.0 | 52.4-69.6 | 50.2-67.9 |
| PD Duration (years) | 2.2 (0.5) | 2.1 (0.5) | 2.6 (0.7) | 1.4 (0.7) | 1.7 (0.5) | 2.7 (0.9) |
| Medicine Use | | | | | | |
| Mean Duration (years) | 2.3 (0.4) | 1.8 (0.4) | 2.7 (0.7) | 1.5 (0.7) | 1.8 (0.3) | 2.1 (0.6) |
| Mean L-dopa equivalents (mg/day) | 453.2 (74.8) | 427.64 (62.0) | 390.9 (102.9) | 469.8 (130.9) | 566.6 (102.6) | 393.5 (46.1) |
| UPDRS Scores | | | | | | |
| Mean Total (ON) | 33.0 (3.9) | 37.7 (3.8) | 36.1 (5.4) | 34.2 (6.6) | 27.8 (5.1) | 40.6 (4.6) |
| Mean UPDRS I | 2.1 (0.4) | 1.5 (0.3) | 1.6 (0.5) | 1.8 (0.6) | 1.3 (0.4) | 2.3 (0.6) |
| Mean UPDRS II (OFF) | 11.2 (1.2) | 10.1 (1.3) | 13.1 (1.5) | 8.2 (1.5) | 8.4 (1.3) | 11.7 (1.5) |
| Mean UPDRS II (ON) | 8.2 (1.5) | 8.1 (1.1) | 9.3 (1.5) | 5.4 (1.9) | 6.3 (1.6) | 10.5 (1.8) |
| Mean UPDRS III (OFF) | 28.3 (2.3) | 30.6 (2.6) | 26.8 (3.3) | 30.2 (4.60) | 30.3 (3.3) | 30.8 (3.3) |
| Mean UPDRS III (ON) | 21.1 (2.9) | 25.2 (2.9) | 24.6 (6.0) | 23.2 (4.0) | 17.5 (4.2) | 25.7 (2.5) |
| Mean UPDRS IV | 2.0 (0.4) | 2.5 (0.8) | 2.0 (0.5) | 2.4 (1.3) | 2.0 (0.6) | 2.2 (1.0) |

ODT = optimized drug therapy,
DBS = deep brain stimulation.
Values represent the mean (SEM).

Example 2

Results

The inventors genotyped subjects enrolled in the Vanderbilt DBS in Early Stage PD clinical trial in which bilateral STN DBS plus medication (hereafter "DBS") was prospectively compared to optimized drug therapy over two years in early-stage PD (Charles et al., 2014). Five of fifteen subjects (33%) in the DBS arm and six of thirteen subjects (46%) in the ODT arm possessed either the heterozygous major allele (Val/Met) or the homozygous minor allele (Met/Met) of the Bdnf variant rs6265 (Table 1).

Figure 3:
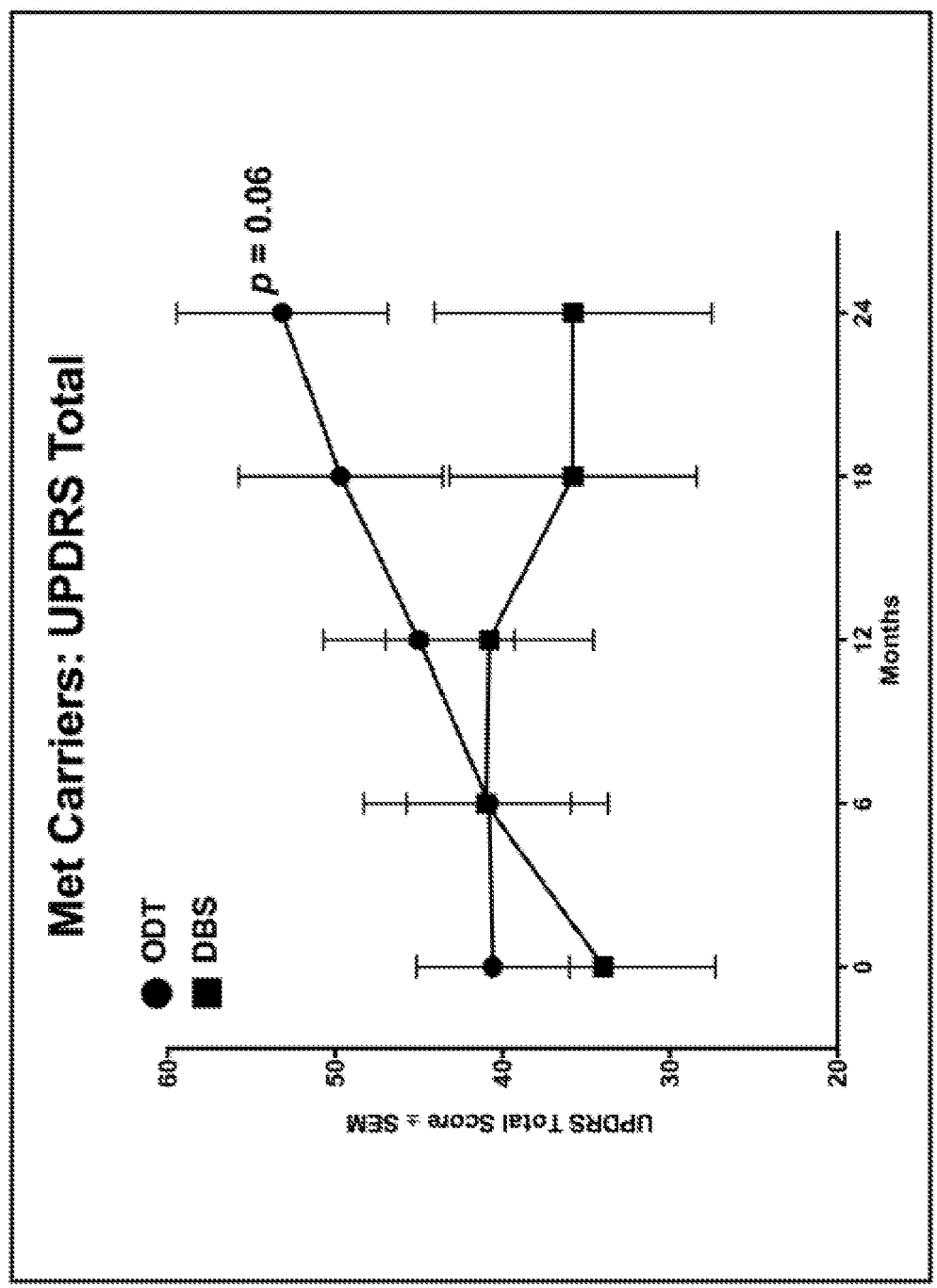
FIG. 3. Met allele carriers may exhibit superior benefit from DBS as measured by UPDRS over 24 Months. Met allele carriers in the ODT arm displayed higher (worse) scores at 24 months compared to Met allele carriers in the DBS arm, though this trend did not reach statistical significance (p=0.06). Values represent the mean±SEM.

At baseline, all clinical endpoints were statistically similar across Bdnf genotypes (Table 1, p>0.05). However, over time Met allele carriers in the ODT treatment arm exhibited significantly higher ON total UPDRS and PDQ-39 scores compared to Val/Val ODT subjects. Specifically, at 18 (p=0.017) and 24 months (p=0.019) UPDRS scores were significantly higher in Met allele carriers compared to Val/Val ODT subjects (FIG. 1A). At 24 months, the UPDRS score of Met allele carrier subjects was ≈20 points higher (Val/Val ODT=33.14±4.34; Met ODT=53.17±6.30). Similarly, Met allele carriers in the ODT arm displayed significantly higher (≈16 points) PDQ-39 scores at 12 (p=0.033) and 24 months (31.80±8.01, p=0.018) compared to Val/Val subjects in the ODT arm (14.97±5.62, FIG. 1B). Possession ODT (FIG. 3), although this difference did not reach statistical significance (p=0.06). Val/Val subjects in the ODT arm exhibited significantly lower (≈6 points) UPDRS-II scores at 24 months (7.43±1.58) compared to Val/Val subjects treated with DBS (13.75±1.77, p=0.016, data not shown).

LEDDs (mg/day) at the end of the study were as follows: DBS Met carriers=491±213; DBS Val/Val=526±65; ODT Met carriers=537±110; and ODT Val/Val=715±101 with no significant differences between treatment groups (p>0.05).

Example 3

Discussion

The Bdnf rs6265 variant confers a functional effect on the activity-dependent release of BDNF (Chen et al., 2006), a neurotrophin that has been implicated in the efficacy of antiparkinsonian therapies (Guillin et al., 2001; Spieles-Engemann et al., 2011; Fischer et al., 2014). Given this variant's prevalence and the heterogeneity of PD patient therapeutic outcomes, the present study sought to test the specific hypothesis that Bdnf rs6265 genotype confers a differential response to ODT or DBS in early-stage PD subjects.

The prevalence of the rs6265 variant in the inventors' patient cohort paralleled the frequency observed in the general population—at least one in three PD subjects. These results indicate that possession of the Bdnf rs6265 Met allele is associated with a less robust response to ODT following 12-18 months of treatment. Specifically, UPDRS scores at 24 months in Met allele ODT subjects were approximately twenty points higher than ODT Val/Val subjects (FIG. 1A), a spread that is considered to be a large clinically important difference (Shulman et al., 2010). Conversely, the Bdnf rs6265 Met allele is not associated with decreased therapeutic benefit from STN DBS. Dopaminergic pharmacotherapy (the primary approach in the ODT subjects) is the predominant treatment for PD over at least the first decade after diagnosis, as STN DBS is not typically offered until after that time. These data suggest that the robustness of a patient's response to medication (i.e., best ON time) during the 'honeymoon' may be predicted by Bdnf variant status.

No association exists between the Bdnf rs6265 variant and PD risk (Zintzaras et al., 2005). In late-stage PD when symptom severity is considerably higher, Bdnf variant status does not appear to affect the limited remaining response to medication (Svetel et al., 2013). However, possession of the Met allele has been associated with the earlier development of levodopa-induced dyskinesia (LID) (Foltynie et al., 2009), suggesting an earlier failure of therapeutic benefit. Of importance, the higher UPDRS score that was observed in ODT Met allele carriers cannot be attributed to LID (FIG. 1A), as UPDRS-IV scores (complications of therapy) were quite low overall with no significant differences observed between any subject cohort (FIGS. 2A-H). This indicates that the suboptimal therapeutic efficacy of Met allele carriers treated with pharmacotherapy precedes the earlier emergence of LID as previously reported. In addition, the very low UPDRS-IV scores suggest that Met allele carriers do not experience a difference in their percentage spent in ON time.

Since this study was a retrospective analysis, stratification by genotype could not be performed, and the data may therefore be subject to bias not addressed through randomization. Met allele carriers on ODT show a lower average LEDD than Val/Val subjects on ODT that could contribute to the different UPDRS-III scores at 24 months; however, the magnitude of difference in LEDDs between these groups was nearly identical at the start compared to the end of the study (144.5 vs. 148.4 mg/day, or expressed as percentages, Met allele carriers were prescribed an average LEDD of 69% and 75% of the Val/Val subjects at 0 and 24 months, respectively). It is unlikely that underlying differences in prescribing practices of the treating neurologists account for all of the variance in the LEDDs between Met allele carriers and Val/Val subjects in the ODT arm. Differences in LEDDs between sub groups were not statistically significant at baseline or at the end of the study. In contrast, there was no significant difference in response to ODT between Val/Val subjects and Met allele carriers at baseline (FIGS. 1 A-D, ≈12 points UPDRS, ≈7 points PDQ-39), but over the course of 24 months these differences were magnified and became significant points UPDRS, (≈22 points UPDRS, ≈18 points PDQ-39).

Pharmacogenetic considerations for PD have previously focused on genes that alter drug metabolism or dopamine transmission (Agundez et al., 2013; Kalinderi et al., 2011). To the inventors' knowledge, surgicogenetic considerations have never been studied for stimulation procedures for PD or other applications. These results suggest that the brain environment created by possession of the Bdnf Met66 allele shapes the response to anti-parkinsonian pharmacotherapy. These finding that the Met66 allele alters the efficacy of anti-parkinsonian medication is analogous to prior studies with antidepressant and antipsychotic treatments (Kocabas et al., 2011; Perkovic et al., 2014), pharmacotherapies that can also be influenced by BDNF signaling.

Preclinical work has implicated BDNF-tropomyosin-related kinase (trkB) signaling in the anti-parkinsonian efficacy of both levodopa and STN DBS (Guillin et al., 2001; Spieles-Engemann et al., 2011; Fischer et al., 2014). Specifically, levodopa administration to unilaterally lesioned rats increases transcript expression of BDNF in the frontal cortex and trkB in the striatum (Guillin et al., 2001). Further, Guillin, et al. (2001) showed that a progressive, levodopa-induced increase in corticostriatal BDNF release was critical to enhanced responsiveness to levodopa and its beneficial effects on motor performance. In a similar PD rat model, STN DBS significantly increased BDNF in the nigrostriatal system and primary motor cortex (Spieles-Engemann et al., 2011), and pharmacologic blockade of trkB attenuated stimulation efficacy (Fischer et al., 2014). The decrease in activity-dependent BDNF release resulting from possession of the Met allele (Chen et al., 2006) may confer a suboptimal, striatal dopaminergic tone that is subsequently insufficient to maintain a prolonged response to dopaminergic medication. Indeed, healthy control subjects with the Met allele display altered striatal dopamine signaling (Pecina et al., 2014). Conversely, the lack of impact the inventors observed of the Met allele on DBS outcomes may be due to the limited involvement of dopaminergic signaling in DBS therapeutic efficacy. Future preclinical studies will examine the potential mechanisms driving the inventors' clinical observations.

These findings demonstrate that in the absence of LID, Bdnf Met66 allele carriers treated with dopaminergic medication experience significantly inferior long-term therapeutic outcomes compared to Val/Val subjects treated with dopaminergic medication; however, variant status does not affect therapeutic response to STN DBS. Although the sample size of the discovery cohort is small, the inventors' data suggest that in ≈40% of the PD population the Bdnf rs6265 Met allele will confer a treatment-specific, suboptimal response to dopaminergic medication that emerges over long treatment intervals. Validation in a larger cohort of early-stage PD subjects treated with dopaminergic medication is warranted to establish whether this phenomenon is truly generalizable to the PD population as a whole. Upon validation, genotyping for the Bdnf variant rs6265 may be used to stratify subjects enrolled in clinical trials and as an important covariate to explain group variances, resulting in more efficient trial designs. Future studies might then examine this variant as a precision medicine approach for the treatment of PD by either medical or surgical interventions.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. References

The following references, to the extent that they provide exemplary procedural or other details supplementary to those set forth herein, are specifically incorporated herein by reference.

Agundez et al., *Expert Opin Drug Metab Toxicol*, 9(7): p. 859-74 (2013).
Ahlskog & Muenter, *Movement Disord.* 16: 448-458 (2001).
Alderborn et al., *Genome Research* 10(8):1249-1258 (2000).
Ausubel et al., Current Protocols in Molecular Biology, John Wiley & Sons, N.Y. (2003).
Bath & Lee, *Cogn Affect Behav Neurosci*, 6(1): p. 79-85 (2006).
Charles et al., *J Parkinsons Dis*, 2(3): p. 215-23 (2012a).
Charles et al., *Parkinsonism Relat Disord*, 18(3): p. 268-73 (2012b).
Charles et al., *Parkinsonism Relat Disord* (2014).
Chen et al., *Genome Research* 9(5):492-498 (1999).
Chen et al., *Science*, 314(5796): p. 140-3 (2006).
Church and Gilbert, *Proc. Natl. Acad. Sci. USA* 81:1991-1995 (1988).
Cotton et al., *Proc. Natl. Acad. Sci. USA* 85:4397-4401 (1985).
Dupont et al., *Control. Clin. Trials* 19: 589-601 (1998).
Eckert et al., *PCR Methods and Applications* 1:17 (1991).
Egan et al., *Cell*, 112(2): p. 257-69, (2003).
Fischer et al., *Mov. Disord.* 29: S438-S429 (2014).
Flavell et al., *Cell* 15:25 (1978).
Foltynie et al., *J Neurol Neurosurg Psychiatry*, 80(2): p. 141-4 (2009).
Geever et al., *Proc. Natl. Acad. Sci. USA* 78:5081 (1981).
Groves et al., *J Appl Physiol.*, 74: 312-318, (1993).
Guatelli et al., *Proc. Nat. Acad. Sci. USA* 87:1874 (1990).
Guillin et al., *Nature* 411: 86-89 (2001).
Hauser et al., *Mov Disord*, 24(16): p. 2328-36 (2009).
Kahn et al., *J Neurol Neurosurg Psychiatry*, 83(2): p. 164-70 (2012).
Kalinderi et al., *Int J Clin Pract*, 65(12): p. 1289-94 (2011).
Kocabas et al., *Int Clin Psychopharmacol*, 26(1): p. 1-10 (2011).
Kwoh et al., *Proc. Natl. Acad. Sci. USA* 86:1173 (1989).
Landegren et al., *Science* 241:1077 (1988).
Maniatis et al., *Proc. Natl. Acad. Sci. USA* 99:2228-2233 (2002).
Mattila et al., *Nucleic Acids Res.* 19:4967 (1991).
McPherson et al., PCR Basics: From Background to Bench, Springer-Verlag, (2000).
Morton et al., *Proc. Natl. Acad. Sci. USA* 98(9):5217-21 (2001).
Myers et al., *Science* 230:1242 (1985).
Nath and Johnson, *Biotechnic. Histochem.* 73(1):6-22 (1998).
Nielsen et al., Bioconjugate Chemistry, The American Chemical Society, 5:1 (1994).
Orita et al., *Proc. Natl. Acad. Sci. USA* 86:2766-2770 (1989).
Pecina et al., *J. Neurosci.* 34: 5874-5881 (2014).
Perkovic et al., *Psychopharmacology*, 231(18): p. 3757-3764 (2014).
Prince et al., *Genome Res.* 11:152-162 (2001).
Raca et al., *Genet Test* 8(4):387-94 (2004).
Saiki et al., *Nature* 324:163-166 (1986).
Samadi et al., *Mov Disord*, 25(1): p. 116-21 (2010).
Sanger et al., *Proc. Natl. Acad. Sci. USA* 74:5463-5467 (1977).
Schafer et al., *Nat. Biotechnol.* 15:33-39 (1995).
Scheupach et al., *NEJM* 368: 610-622 (2013).
Sheffield et al., *Proc. Natl. Acad. Sci. USA* 86:232-236 (1989).
Shulman et al., *Arch Neurol*, 67(1): p. 64-70 (2010).
Spieles-Engemann et al., *J Parkinsons Dis*, 1(1): p. 123-136 (2011).
Stoneking et al., *Am. J. Hum. Genet.* 48:370-382 (1991).
Svetel et al, *Eur. Neurol.* 70: 257-262 (2013).
Tanner et al., *NEJM* 368: 675-676 (2013)
Tapper et al., *Proc. Natl. Acad. Sci. USA* 102(33):11835-11839 (2005).
The International HapMap Consortium, *Nature* 426:789-796 (2003).
The International HapMap Consortium, *Nature* 437:1299-1320 (2005).
Tomlinson et al., *Mov Disord*, 25(15): p. 2649-53 (2010).
U.S. Pat. No. 4,683,195
U.S. Pat. No. 4,683,202
U.S. Pat. No. 5,288,644
U.S. Pat. No. 5,491,224
U.S. Pat. No. 5,776,688
U.S. Pat. No. 5,800,998
U.S. Patent Publication No. 2004/0014095
Underhill et al., *Genome Res.* 7:996-1005 (1997).
Wang et al., *Am J Respir Cell Mot Biol.*, 29:465-71 (2003).
Weaver et al., *Neurology*, 79(1): p. 55-65 (2012).
Wheeless et al., *Cytometry* 17:319-326 (1994).
WO 99/57318
Wu and Wallace, *Genomics* 4:560 (1989).
Zintzaras & Hadjigeorgiou, *J Hum Genet*, 50(11): p. 560-6, (2005).

What is claimed is:

1. A method of treating an early stage Parkinson's disease patient with deep brain stimulation (DBS) and optimized drug therapy (ODT) comprising:
   (a) subjecting a nucleic acid containing sample from an early stage Parkinson's disease patient to sequence analysis;
   (b) determining the presence or absence of a single nucleotide polymorphism resulting in a Val to Met substitution in the brain derived neurotrophic factor (BDNF) gene coding for residue 66;
   (c) identifying the patient as a non-long term responder to ODT when the nucleic acid containing sample exhibits a Val/Met or Met/Met profile; and
   (d) treating said patient with DBS+ODT when said nucleic acid containing sample exhibits a Val/Met or Met/Met profile;
   wherein the early stage Parkinson's disease patient is defined as having idiopathic Parkinson's disease, on antiparkinsonian medications for less than four years, and without a history of motor fluctuations and dyskinesias.

2. The method of claim 1, wherein said nucleic acid containing sample is a DNA sample.

3. The method of claim 1, wherein said nucleic acid-containing sample is an RNA sample.

4. The method of claim 1, wherein said nucleic acid-containing sample is a tissue sample including, but not limited to, urine, cerebrospinal fluid, saliva, serum, skin, biopsy, biopsy of any organ, blood, semen, stool, ova, hair, hair follicle, or a mucosal cell.

5. The method of claim 1, wherein said sequence analysis comprises PCR, primer extension, site specific amplification, site specific hybridization, site specific cleavage, ligation, pyrosequencing, SNP microarray, mini-sequencing, RNA seq, real time sequencing, ion or torrent pH sensing.

6. The method of claim 1, further comprising preparing a report corresponding to step (c).

\* \* \* \* \*